US008119138B2

(12) United States Patent  
Sirbasku

(10) Patent No.: US 8,119,138 B2
(45) Date of Patent: Feb. 21, 2012

(54) ANTI-ESTROGEN AND IMMUNE MODULATOR COMBINATIONS FOR TREATING BREAST CANCER

(75) Inventor: David A. Sirbasku, Houston, TX (US)

(73) Assignee: Signe Biopharma Inc., Irving, TX (US)

( * ) Notice: Subject to any disclaimer, the term of this patent is extended or adjusted under 35 U.S.C. 154(b) by 847 days.

(21) Appl. No.: 10/293,439

(22) Filed: Nov. 13, 2002

(65) Prior Publication Data

US 2003/0072760 A1 Apr. 17, 2003
US 2010/0303825 A9 Dec. 2, 2010

Related U.S. Application Data

(63) Continuation-in-part of application No. 09/852,958, filed on May 10, 2001, now Pat. No. 7,947,275, and a continuation-in-part of application No. 09/852,547, filed on May 10, 2001, now Pat. No. 7,947,463.

(60) Provisional application No. 60/231,273, filed on Sep. 8, 2000, provisional application No. 60/229,071, filed on Aug. 30, 2000, provisional application No. 60/208,111, filed on May 31, 2000, provisional application No. 60/208,348, filed on May 31, 2000, provisional application No. 60/203,314, filed on May 10, 2000, provisional application No. 60/332,801, filed on Nov. 14, 2001.

(51) Int. Cl.
A61K 31/137 (2006.01)
A61K 31/202 (2006.01)
A61K 31/56 (2006.01)
A61K 39/395 (2006.01)

(52) U.S. Cl. .................. 424/155.1; 514/170; 514/560; 514/649

(58) Field of Classification Search .............. 424/155.1; 514/170, 560, 649
See application file for complete search history.

(56) References Cited

U.S. PATENT DOCUMENTS

| 4,849,508 | A | 7/1989 | Magnin et al. |
|---|---|---|---|
| 4,859,585 | A | 8/1989 | Sonnenschein et al. |
| 4,919,937 | A | 4/1990 | Mauvais-Jarvis et al. |
| 5,075,425 | A | 12/1991 | Kotitschke et al. |
| 5,135,849 | A | 8/1992 | Soto |
| 5,405,772 | A | 4/1995 | Ponting |
| 6,200,547 | B1 | 3/2001 | Volkonsky et al. |
| 2002/0006630 | A1 | 1/2002 | Sirbasku |
| 2003/0017445 | A1* | 1/2003 | Berg et al. .......... 435/4 |

FOREIGN PATENT DOCUMENTS

| EP | 0702960 A1 | 3/1996 |
|---|---|---|
| WO | WO92/13563 | 8/1992 |
| WO | WO98/04681 | 2/1998 |
| WO | WO98/08934 | 3/1998 |

OTHER PUBLICATIONS

Ariazi et al (Cancer Research 62:6510-6518 (Nov. 15, 2002).*
Coward et al. (PNAS 98:8880-8884 (Nov. 17, 2001).*
Stern et al. (Cancer Immunol Immunother. 19:226-230 (1985).*
Fridman FASEB J. 5:2684-2690 (1991).*
Krajci et al. Eur. J. Immunol. 22:2309-2315 (1992) Abstract.*
Smith et al. (Nature Biotechnology 15:1222-1223 (1997)).*
Brenner (Trends in Genetics 15:132-133 (1999)).*
Moraru et al. (FEBS Letts. 274:93-95 (1990).*
PCT International Search Report, PCT/US01/15183 dated 20/112002, 3 pages.
Zhihong Chen et al., A serum-free medium for hybridoma cell culture, Cytotechnology (1993), vol. 11, pp. 169-174, XP001117870, ISSN: 0920-9069 p. 170, media and additives; pp. 173-174.
Database Biosis 'Online! Biosciences Information Service, Philadelphia, PA US; 1992, Eby J.E. et al., Preparation of Iron-Deficient Tissue Culture Medium by Deferoxamine-Sepharose Treatment and Application to the Differential Actions of Apotransferrin and Differic Transferrin, Database assession No. PREV199294057133, XP002218819 cited in the application abstract & Analytical Biochemistry, vol. 203, No. 2, 1992, pp. 317-325, ISSN:0003-2697.
Database Biosis 'Online! Biosciences Information Service, Philadelphia, PA US 1993, Eby John E. et al., Apotransferrin stimulation of thyroid hormone dependent rat pituitary tumor cell growth in serum-free chemically defined medium: Role of iron(III) chelation, Database accession No. PREV199396113609, XP002218820 cited in application abstract & Journal of Cellular Physiology, vol. 156, No. 3, 1993, pp. 588-600, ISSN:0021-9541.
Neumannova Vera et al., Growth of human tumor cell lines in transferrin-free, low-iron medium, In Vitro Cellular & Developmental Biology Animal, vol. 31, No. 8, 1995, pp. 625-632, XP001118629, ISSN:1071-2690, the whole document.
C.A. Janeway et al., Chapter 3: Structure of the Antibody Molecule and the Immunoglobulin Genes: Structural variation in immunoglobulin constant regions; Chapter 9: The Humoral Immune Response: The distribution and functions of immunoglobulin isotypes, Immuno. Biology—The Immune System in Health and Disease, Fourth Edition, Elsevier Science Ltd./Garland Publishing (1999) pp. 104, 326-327.

(Continued)

Primary Examiner — Lynn Bristol
(74) Attorney, Agent, or Firm — Merchant & Gould P.C.; Brian R. Dorn

(57) ABSTRACT

Compositions for treating cancers of mucosal tissues including breast, prostate, ovary, colon are disclosed which include various combinations of new or conventional anti-estrogen compounds, aromatase inhibitors, immune modulators, immune inhibitors, immune inhibitor mimicking compounds and steroid or thyroid hormones. Methods of predicting susceptibility of a cancer of mucosal origin to treatment with a composition containing an immune inhibitor or an immune inhibitor mimicking compound are also disclosed. Preferred methods include identifying in a specimen of cancer cells the presence of a Poly-Ig (Fc) receptor or Poly-Ig-like (Fc) receptor capable of binding to an immune inhibitor or an immune inhibitor mimicking compound and of mediating immune inhibition of cancer cell growth.

2 Claims, No Drawings

OTHER PUBLICATIONS

R.G. Hamilton, *Chapter 3: Human Immunoglobulins*, Handbook of Human Immunology, CRC Press LLC (1997) pp. 65-109.

A.J. Alberg et al., *Epidemiology, prevention, and early detection of breast cancer [Breast]*, Current Opinion in Oncology (Nov. 1997) vol. 9, 6, pp. 505-511, PMID: 9370070 [PubMed—indexed for Medline]; Abstract http://www.ncbi.nlm.nih.gov/entrez/query.fcgi?cmd=Retrieve&db=PubMed&list_uids=9370070&d... printed on Feb. 15, 2003 (1 page).

A.J. Alberg et al., *Epidemiology, prevention, and early detection of breast cancer [Breast]*, Current Opinion in Oncology (Nov. 1999) vol. 11, No. 6, pp. 435, 13 pages.

J.C. Allegra et al., *Growth of a Human Breast Cancer Cell Line in Serum-Free Hormone-Supplemented Medium*, Cancer Research (Nov. 1978) vol. 38, pp. 3823-3829.

J.F. Amara et al., *17β-Estradiol Has a Biphasic Effect on GH Cell Growth*, Endocrinology, Dept. of Pharm., Endocrinology (Mar. 1983) vol. 112, No. 3, pp. 1141-1143.

T. Anttila et al., *Serotypes of Chlamydia Trachomatis and Risk for Development of Cervical Squamous Cell Carcinoma*, JAMA (Jan. 2001) vol. 285, No. 1, pp. 47-51, PMID: 11150108 [PubMed—indexed for Medline]; Abstract http://www.ncbi.nlm.nih.gov/entrez/query.fcgi?cmd=Retrieve&db=PubMed&list_uids=11150108&d... printed on Feb. 15, 2003 (2 pages).

T. Anttila et al., *Serotypes of Chlamydia Trachomatis and Risk for Development of Cervical Squamous Cell Carcinoma*, JAMA (Jan. 2001) vol. 285, No. 1, pp. 47-51, (Original Contribution) 11 pages.

J.M. Zenilman, *Chlamydia and Cervical Cancer: A Real Association?* JAMA (Jan. 2001) 285, No. 1, pp. 81-83, (Editorial) 5 pages.

P.E. Gravitt et al., *Chlamydia trachomatis and Cervical Squamous Cell Carcinoma*, JAMA (Apr. 2001) vol. 285, No. 13, pp. 1703-1706, (Letters) 11 pages.

B.A. Arrick, *Therapeutic implications of the TGF-beta system*, J. Mammary Gland Biol. Neoplasia. (Oct. 1996) 1(4):391-7, PMID: 10887513 [PubMed—indexed for Medline]; Abstract http://www.ncbi.nlm.nih.gov/entrez/query.fcgi?cmd=Retrieve&db=PubMed&list_uids=10887513&d... printed on Feb. 21, 2003 (1 page).

C.L. Arteaga et al., *Blockade of the Epidermal Growth Factor Receptor Inhibits Transforming Growth Factor α-Induced but Not Estrogen-Induced Growth of Hormone-Dependent Human Breast Cancer*, Molecular Endocrinology (Nov. 1988) vol. 2, No. 1 pp. 1064-1069.

C.L. Arteaga et al., *Blockade of the Type I Somatomedin Receptor Inhibits Growth of Human Breast Cancer Cells in Athymic Mice*, J. Clin. Invest. (Nov. 1989) vol. 84, pp. 1418-1423.

C.L. Arteaga et al., *The multifunctional role of transforming growth factor (TGF)-beta s on mammary epithelial cell biology*, Breast Cancer Res. Treat. 1996; 38(1):49-56, PMID: 8825122 [PubMed—indexed for Medline]; Abstract; http://www.ncbi.nlm.nih.gov/entrez/query.fcgi?cmd=Retrieve&db=PubMed&list_uids=8825122&d... printed on Feb. 21, 2003 (1 page).

C.L. Arteaga et al., *Transforming Growth factor beta: potential autocrine growth inhibitor of estrogen receptor-negative human breast cancer cells*, Breast Cancer Res Treat. (Jul. 1998) 48(14):3898-904, PMID: 3164252 [PubMed—indexed for Medline]; Abstract; http://www.ncbi.nlm.nih.gov/entrez/query.fcgi?cmd=Retrieve&db=PubMed&list_uids=3164252&d... printed on Feb. 21, 2003 (2 pages).

A.M. Soto, *The Role of Estrogens on the Proliferation of Human Breast Tumor Cells (MCF-7)*, J. Steroid Biochem. (1985) vol. 23, No. 1, pp. 87-94.

M.A. Bakos et al., *Expression and purification of biologically active domain I of the human polymeric immunoglobulin receptor*, Mol. Immunol. (Feb. 1994) 31(2):165-8, PMID: 8309479 [PubMed—indexed for Medline]; Abstract; http://www.ncbi.nlm.nih.gov/entrez/query.fcgi?cmd=Retrieve&db=PubMed&list_uids=8309479&d... printed on Feb. 22, 2003, 1 page.

M.A. Bakos et al., *Characterization of a critical binding site for human polymeric Ig on secretory component*, J. Immunol. (Nov. 1991) 147(10):3419-26, PMID: 1940346 [PubMed—indexed for Medline]; Abstract Http://www.ncbi.nlm.nih.gov/entrez/query.fcgi?cmd=Retrieve&db=PubMed&list_uids=1940346&d... printed on Feb. 20, 2003, 1 page.

M.A. Bakos et al., *A Conserved Binding Site on the Receptor for Polymeric Ig Is Homologous to CDRI of Ig Vk Domains*, J. Immunol. (Aug. 1993) vol. 151, No. 3, pp. 1346-1352.

D. Barnes et al., *Growth of a human mammary tumour cell line in a serum-free medium*, Nature, Macmillan Journals Ltd. (Oct. 1979) vol. 281, No. 5730, pp. 388-389.

J. Baselga et al., *Phase II study of weekly intravenous recombinant humanized anti-p185HER2 monoclonal antibody in patients with HER2/neu-overexpressing metastatic breast cancer*, Comment in J. Clin. Oncol. (Mar. 1996) vol. 14, No. 3, pp. 697-699, PMID: 8622019 [PubMed—indexed for Medline]; Abstract, http://www.ncbi.nlm.nih.gov/entrez/query.fcgi?cmd=Retrieve&db=PubMed&list_uids=8622019&dc printed on Feb. 22, 2003, 2 pages.

V. Beral et al., *Overview of the Epidemiology of Immunodeficiency—Associated Cancers*, J. Natl. Cancer Inst. Monogr. (1998) No. 23, pp. 1-6.

P. Brandtzaeg et al., *Immunoglobulin M: Local Synthesis and Selective Secretion in patients with Immunoglobulin A Deficiency*, Science (Mar. 1968) vol. 160, pp. 789-791.

Y. Berthois et al., *Phenol red in tissue culture media is a weak estrogen.- Implications concerning the study of estrogen-responsive cells in culture*, Proc. Natl. Acad. Sci. USA (Apr. 1986) vol. 83, No. 8, pp. 2496-2500.

S. Bhatia et al., *Breast Cancer and Other Second Neoplasms after Childhood Hodgkin's Disease*, N. Engl. J. Med., Mar. 21, 1996, vol. 334, No. 12, pp. 745-751 (Original Articles), 15 pages.

S.S. Donaldson et al., *Second Cancers after Hodgkin's Disease in Childhood*, N. Engl. J. Med., Mar. 21, 1996, vol. 334, No. 12, pp. 792-794 (Editorials), 4 pages.

F.E. Mirer et al., *Late Effects of Treatment for Childhood Hodgkin's Disease*, N. Engl. J. Med., Aug. 1, 1996, vol. 335, No. 5, pp. 352-355 (Correspondence), 12 pages.

I. Bieche et al., *Loss and gain of distinct regions of chromosome 1q in primary breast cancer*, Clin. Cancer Res. (Jan. 1995) vol. 1, No. 1, pp. 123-127, PMID: 9815894 [PubMed—indexed for Medline], Abstract, http://www.ncbi.nlm.nih.gov/entrez/query/fcgi?cmd=Retrieve&db=PubMed&list_uids=9815894&dc..., printed on Feb. 21, 2003, 1 page.

I. Bieche et al., *Deletion mapping of Chromosomal Region 1p32-pter in Primary Breast Cancer*, Genes, Chromosomes & Cancer (Mar. 1999), vol. 24, No. 3, pp. 255-263.

R.D. Bindal et al., *Bis(4-hydroxyphenyl)(2-(phenoxysulfonyl)phenyl)methane: Isolation and Structure Elucidation of a Novel Estrogen from Commercial Preparations of Phenol Red (Phenolsulfonphthalein)*, J. Med. Chem. (Oct. 1988) vol. 31, No. 10, pp. 1978-1983.

R.D. Bindal et al., *Lipophilic Impurities, Not Phenolsulfonphthalein, Account for the Estrogenic Activity in Commercial Preparation of Phenol Red*, J. Steroid Biochem (Sep. 1988) vol. 31, No. 3, pp. 287-293).

W.P. Bocchinfuso et al., *Mammary gland development and tumorigenesis in estrogen receptor knockout mice*, J. Mammary Gland Biol. Neoplasia (Oct. 1977) vol. 2, No. 4, pp. 323-334, PMID: 10935020 [PubMed—indexed for Medline], Abstract, http://www.ncbi.nlm.nih.gov/enrez/query.fcgi?cmd=Retrieve&db=PubMed&list_uids=109335020&... printed on Feb. 21, 2003, 1 page.

E. Boder, *Ataxia-telangiectasia: some historic, clinical and athologic observations*, Birth Defects Orig. Artic. Ser. 1975;11(1):255-70, PMID: 1096982 [PubMed—indexed for Medline], Abstract, http://www.ncbi.nlm.nih.gov/enrez/query.fcgi?cmd=Retrieve&db=PubMed&list_uids=1096982&... printed on Feb. 12, 2003, 1 page.

P. Bordigoni et al., *Improvement of cellular immunity and IgA production in immunodeficient children after treatment with synthetic serum thymic factor (FTS)*, Lancet (Aug. 1982) vol. 2, No. 8293, pp. 293-297, PMID: 6124716 [PubMed—indexed for Medline], Abstract, http://www.ncbi.nlm.nih.gov/enrez/query.fcgi?cmd=Retrieve&db=PubMed&list_uids=6124716&... printed on Feb. 12, 2003, 1 page.

P.N. Boyaka et al., *Strategies for mucosal vaccine development*, Am. J. Trop. Med. Hyg (Apr. 1999) vol. 4 Supple., pp. 35-45, PMID: 10344675 [PubMed—indexed for Medline], Abstract, http://www.

ncbi.nlm.nih.gov/enrez/query.fcgi?cmd=Retrieve&db=PubMed&list_uids=10344675&... printed on Feb. 21, 2003, 1 page.

P. Brandtzaeg, *Role of J Chain and Secretory Component in Receptor-Mediated Glandular and Hepatic Transport of Immunoglobulins in Man*, Scand. J. Immunol. (Aug. 1985) vol. 22, No. 2, pp. 111-146.

P. Brandtzaeg, *Part IV. Transport of IgA and the Role of the Liver: The Secretory Immune System of Lactating Human Mammary Glands Compared With Other Exocrine Organs*, Annals N.Y. Acad. Sciences (Jun. 1983) vol. 409, pp. 353-382.

P. Brandtzaeg, *Immunoglobulin M: local synthesis and selective secretion in patients with immunoglobulin A deficiency*, Science (May 1968) vol. 160, No. 829, pp. 789-791, PMID 4171541 [PubMed—indexed for Medline], Abstract, http://www.ncbi.nlm.nih.gov/enrez/query.fcgi?cmd=Retrieve&db=PubMed&list_uids=4171541&... printed on Feb. 12, 2003, 1 page.

P. Brandtzaeg, *The secretory immune system of lactating human mammary glands compared with other exocrine organs*, Annals N.Y. Acad. Sciences (Jun. 1983) vol. 409, pp. 353-82, PMID 6408971 [PubMed—indexed for Medline], Abstract, http://www.ncbi.nlm.nih.gov/enrez/query.fcgi?cmd=Retrieve&db=PubMed&list_uids=6408971&... printed on Feb. 20, 2003, 1 page.

P. Brandtzaeg et al., *Direct evidence for an integrated function of J chain and secretory component in epithelial transport of immunoglobulins*, Nature (Sep. 1984) vol. 311, No. 5981, pp. 71-73.

P. Brandtzaeg, *Molecular and cellular aspects of the secretory immunoglobulin system*, APMIS (Jan. 1995) vol. 103, No. 1, pp. 1-19, PMID 7695886 [PubMed—indexed for Medline], Abstract, http://www.ncbi.nlm.nih.gov/enrez/query.fcgi?cmd=Retrieve&db=PubMed&list_uids=7695886&... printed on Feb. 22, 2003, 1 page.

D.A. Bronzert et al., *Transforming growth factor-beta induces platelet-derived growth factor (PDGF) messenger RNA and PDGF secretion while inhibiting growth in normal human mammary epithelial cells*, Mol. Endocrinol (Jul. 1990) vol. 4, No. 7, pp. 981-989, PMID 2178225 [PubMed—indexed for Medline], Abstract, http://www.ncbi.nlm.nih.gov/enrez/query.fcgi?cmd=Retrieve&db=PubMed&list_uids=2178225&... printed on Feb. 19, 2003, 1 page.

M.G. Brattain et al., *Defects of TGF-beta receptor signaling in mammary cell tumorigenesis*, J. Mammary Gland Biol. Neoplasia (Oct. 1996) vol. 1, No. 4, pp. 365-372, PMID 10887510 [PubMed—indexed for Medline], Abstract, http://www.ncbi.nlm.nih.gov/enrez/query.fcgi?cmd=Retrieve&db=PubMed&list_uids=10887510&... printed on Feb. 21, 2003, 1 page.

J.W. Brewer et al., *Mechanism and subcellular localization of secretory IgM polymer assembly*, J. Biol. Chem. (Jun. 1994) vol. 269, No. 25, pp. 17338-17348.

P. Briand et al., *Long-Term Cultivation of a Human Breast Cancer Cell Line, MCF-7, in a Chemically Defined Medium. Effect of Estradiol*, Anticancer Research (Jan.-Feb. 1986) vol. 6, No. 1, pp. 85-90.

J. Brolin et al., *Immunohistochemistry and biochemistry in detection of androgen, progesterone, and estrogen receptors in benign and malignant human prostatic tissue*, Prostate (1992) vol. 20, No. 4, pp. 281-295, PMID 1376911 [PubMed—indexed for Medline], Abstract, http://www.ncbi.nlm.nih.gov/enrez/query.fcgi?cmd=Retrieve&db=PubMed&list_uids=1376911&... printed on Feb. 20, 2003, 1 page.

J.C. Cambier, *Inhibitory receptors abound?* Proc. Natl. Acad. Sci. USA (Jun. 1997) vol. 94, No. 12, pp. 5993-5995.

L.A. Castagnetta et al., *Human prostate cancer: a direct role for oestrogens*, Ciba Found Symp (1995) vol. 191, pp. 269-286; discussion pp. 286-289, PMID 8582203 [PubMed—indexed for Medline], Abstract, http://www.ncbi.nlm.nih.gov/enrez/query.fcgi?cmd=Retrieve&db=PubMed&list_uids=8582203&... printed on Feb. 20, 2003, 1 page.

D. Chakravarthy et al., *Expression and secretion of TGF-beta isoforms and expression of TGF-beta-receptors I, II, and III in normal and neoplastic human breast*, Int. J. Oncol. (Jul. 1999) vol. 15, No. 1, pp. 187-194, PMID 10375614 [PubMed—indexed for Medline], Abstract, http://www.ncbi.nlm.nih.gov/enrez/query.fcgi?cmd=Retrieve&db=PubMed&list_uids=10375614&... printed on Feb. 22, 2003, 1 page.

D. Chalbos et al., *Estrogens stimulate cell proliferation and induce secretory proteins in a human breast cancer cell line (T47D)*, J. Clin. Endocrinol. Metab. (Aug. 1982) vol. 55, No. 2, pp. 276-283.

T.R. Chen et al., *WiDr is a derivative of another colon adenocarcinoma cell line, HT-29*, Cancer Genet Cytogenet (Jul. 1987) vol. 1, pp. 125-134, PMID 3472642 [PubMed—indexed for Medline], Abstract, http://www.ncbi.nlm.nih.gov/enrez/query.fcgi?cmd=Retrieve&db=PubMed&list_uids=3472642&... printed on Feb. 19, 2003, 1 page.

M.E. Conley et al., *Intravascular and mucosal immunoglobulin A: two separate but related systems of immune defense?* Ann Intern Med. (Jun. 1987) vol. 106, No. 6, pp. 892-899, PMID 3579073 [PubMed—indexed for Medline], Abstract, http://www.ncbi.nlm.nih.gov/enrez/query.fcgi?cmd=Retrieve&db=PubMed&list_uids=3579073&... printed on Feb. 22, 2003, 1 page.

P. Corvol et al., *Species Distribution of Testosterone-Binding Globulin*, Biol. Reprod. (Apr. 1973) vol. 8, No. 3, pp. 277-282.

J.F. Couse et al., *Estrogen Receptor Null Mice: What Have We Learned and Where Will They Lead Us?* Endocrine Reviews (Jun. 1999) vol. 20, No. 3, pp. 358-417.

M. Daeron, *Fc Receptor Biology*, Annu. Rev. Immunol. (1997) vol. 15, pp. 203-234.

D.A. Damassa et al., *Biological Effects of Sex Hormone-Binding Globulin on Androgen-Induced Proliferation and Androgen Metabolism in LNCaP Prostate Cells*, Endocrinology (Jul. 1991) vol. 29, No. 1, pp. 75-84.

C.W. Daniel et al., *The role of TGF-beta in patterning and growth of the mammary ductal tree*, J. Mammary Gland Biol. Neoplasia (Oct. 1996) vol. 1, No. 4, pp. 331-341, PMID 10887507 [PubMed—indexed for Medline], Abstract, http://www.ncbi.nlm.nih.gov/enrez/query.fcgi?cmd=Retrieve&db=PubMed&list_uids=10887507&... printed on Feb. 21, 2003, 1 page.

D. Danielpour et al, *Growth of MTW9/PL2 Estrogen-Responsive Rat Mammary Tumor Cells in Hormonally Defined Serum-Free Media*, In Vitro Cell Dev. Biol. (Jan. 1988) vol. 24, No. 1, pp. 42-52.

P. Darbre et al., *Effect of Estradiol on Human Breast Cancer Cells in Culture*, Cancer Research (Jan. 1983), vol. 43, No. 1, pp. 349-354.

P.D. Darbre et al., *Effects of Estradiol and Tamoxifen on Human Breast Cancer Cells in Serum-free Culture*, Cancer Research (Jul. 1984) vol. 44, No. 7, pp. 2790-2793.

G. Del Giudice et al., *Mucosal Delivery of Vaccines*, Methods (Sep. 1999) vol. 19, No. 1, pp. 148-155.

R.B. Dickson et al., *Estrogenic Regulation of Growth and Polypeptide Growth Factor Secretion in Human Breast Carcinoma*, Endocrine Reviews (Feb. 1987) vol. 8, No. 1, pp. 29-43.

R.B. Dickson et al., *Induction of epidermal growth factor-related polypeptides by 17 beta-estradiol in MCF-7 human breast cancer cells*, Endocrinology (Jan. 1986) vol. 118, No. 1, pp. 138-142, PMID 3000728 [PubMed—indexed for Medline], Abstract, http://www.ncbi.nlm.nih.gov/enrez/query.fcgi?cmd=Retrieve&db=PubMed&list_uids=3000728&... printed on Feb. 19, 2003, 1 page.

R.B. Dickson et al., *Chapter 8: Estrogen Receptor-Mediated Processes in Normal and Cancer Cells*, J. Natl. Cancer Inst. Monogr. (2000) No. 27, pp. 135-145.

C.T. Eastment et al., *Human Platelet lysate Contains Growth Factor Activities for Established Cell Lines Derived From Various Tissues of Several Species*, in Vitro (1980) vol. 16, No. 8, pp. 694-705.

J.E. Eby et al., *Apotransferrin Stimulation of Thyroid Hormone Dependent Rat Pituitary Tumor Cell Growth in Serum-Free Chemically Defined Medium: Role of Fe(III) Chelation*, J. Cellular Physiology (Sep. 1993) vol. 156, No. 3, pp. 588-600.

J.E. Eby et al., *Preparation of Iron-Deficient Tissue Culture Medium by Deferoxamine-Sepharose Treatment and Application to the Differential Actions of Apotransferrin and Differric Transferrin*, Anal. Biochem. (Jun. 1992) vol. 203, No. 2, pp. 317-325.

K. el-Bayoumy et al., *Comparative tumorigenicity of benzo[a]pyrene, 1-nitropyrene and 2-amino-l-methyl-6-phenylimidazo[4,5-b]pyridine administered by gavage to female CD rats*, Carcinogenesis (Feb. 1995) vol. 16, No. 2, pp. 431-434.

L.W. Engel et al., *Establishment and Characterization of Three New Continuous Cell Lines Derived from Human Breast Carcinomas*, Cancer Research (Oct. 1978), vol. 38, No. 10, pp. 3352-3364.

E. Enmark et al. *Oestrogen receptors—an overview*, J. Intern. Med. (Aug. 1999) No. 146, pp. 133-138.

E. Enmark et al., *Human Estrogen Receptor β-Gene Structure, Chromosomal Localization, and Expression Pattern*, J. Clin. Endocrinol. Metab. (Dec. 1997) vol. 82 No. 12, pp. 4258-4265.

R.H. Evans, *The Steroid and Thyroid Hormone Receptor Superfamily*, Science (May 1988) vol. 240, No. 4854, pp. 889-895, PMID 3283939 [PubMed—indexed for Medline], Abstract, http://www.ncbi.nlm.nih.gov/enrez/query.fcgi?cmd=Retrieve&db=PubMed&list_uids=3283939&... printed on Feb. 20, 2003, 1 page.

E. Fallgreen-Gebauer et al., *The covalent Linkage of Secretory Component to IgA. Structure of sIgA*, Biol. Chem. (Nov. 1993) vol. 374, No. II, pp. 1023-1028.

P. Fernlund et al., *A Simple Two-Step Procedure for the Simultaneous Isolation of Corticosteroid Binding Globulin and Sex Hormone Binding Globulin from Human Serum by Chromatography on Cortisol-Sepharose and Phenyl-Sepharose*, J. Steroid Biochem (Jun. 1981) vol. 14, No. 6, pp. 545-552.

L. Fiore et al., *Poliovirus Sabin Type 1 Neutralization Epitopes Recognized by Immunoglobulin a Monoclonal Antibodies*, J. Virol. (Sep. 1997) vol. 71, No. 9, pp. 6905-6912.

B. Fisher et al., *Tamoxifen for Prevention of Breast Cancer: Report of the National Surgical Adjuvant Breast and Bowel Project P-1 Study*, J. Natl. Cancer Inst., Articles (Sep. 1998) vol. 90, No. 18, pp. 1371-1388.

W.H. Fridman, *Fc receptors and immunoglobulin binding factors*, FASEB J. (Sep. 1991) vol. 5, No. 12, pp. 2684-2690, PMID 1916092 [PubMed—indexed for Medline], Abstract, http://www.ncbi.nlm.nih.gov/enrez/query.fcgi?cmd=Retrieve&db=PubMed&list_uids=1916092&... printed on Feb. 15, 2003, 1 page.

S.A. Fuqua et al., *Variant human breast tumor estrogen receptor with constitutive transcriptional activity*, Cancer Res. (Jan. 1991) vol. 51, No. 1, pp. 105-109, PMID 1988075 [PubMed—indexed for Medline], Abstract, http://www.ncbi.nlm.nih.gov/enrez/query.fcgi?cmd=Retrieve&db=PubMed&list_uids=1988075&... printed on Feb. 20, 2003, 1 page.

S.A. Fuqua et al., *Inhibition of estrogen receptor action by a naturally occurring variant in human breast tumors*, Cancer Res. (Jan. 1992) vol. 52, No. 2, pp. 483-486, PMID 1728420 [PubMed—indexed for Medline], Abstract, http://www.ncbi.nlm.nih.gov/enrez/query.fcgi?cmd=Retrieve&db=PubMed&list_uids=1728420&... printed on Feb. 20, 2003, 1 page.

S.A. Fuqua et al., *Expression of Wild-Type Estrogen Receptor Beta and Variant Isoforms in Human Breast Cancer*, Cancer Res. (Nov. 1999) vol. 59, No. 21, pp. 5425-5428.

R.W. Furlanetto et al., *Somatomedin-C Receptors and Growth Effects in Human Breast Cells Maintained in Long-Term Tissue Culture*, Cancer Res. (May 1984) vol. 44, No. 5, pp. 2122-2128.

V. Giguere et al., *Identification of a new class of steroid hormone receptors*, Nature (Jan. 1988) vol. 331, No. 6151, pp. 91-94, PMID 3267207 [PubMed—indexed for Medline], Abstract, http://www.ncbi.nlm.nih.gov/enrez/query.fcgi?cmd=Retrieve&db=PubMed&list_uids=3267207&... printed on Feb. 12, 2003, 1 page.

H. Gobbi et al., *Transforming Growth Factor-Beta and Breast Cancer Risk in Woman With Mammary Epithelial Hyperplasia*, J. Natl. Cancer Inst. (Dec. 1999) vol. 91, No. 24, pp. 2096-2101.

D. Gospodarowicz et al., *Heparin protects basic and acidic FGF from inactivation*, J. Cell Physiol. (Sep. 1986) vol. 128, No. 3, pp. 475-484, PMID 3528177 [PubMed—indexed for Medline], Abstract, http://www.ncbi.nlm.nih.gov/enrez/query.fcgi?cmd=Retrieve&db=PubMed&list_uids=3528177&... printed on Feb. 20, 2003, 1 page.

M.L. Graham et al., *T47DCO cells, genetically unstable and containing estrogen receptor mutations, are a model for the progression of breast cancers to hormone resistance*, Cancer Res. (Oct. 1990) vol. 50, No. 19, pp. 6208-6217, PMID 2400987 [PubMed—indexed for Medline], Abstract, http://www.ncbi.nlm.nih.gov/enrez/query.fcgi?cmd=Retrieve&db=PubMed&list_uids=2400987&... printed on Feb. 20, 2003, 1 page.

J.A. Gustafsson, *Seeking Ligands for Lonely Orphan Receptors*, Science (May 1999) 284(5418):1285-6, Science (May 1999) 284(5418):1362-5, Science (May 1999) 284(5418):1365-8.

J.A. Gustafsson, *Estrogen receptor beta—a new dimension in estrogen mechanism of action*; J. Endocrinol (Dec. 1999) vol. 163, No. 3, pp. 379-383.

J.A. Gustafsson et al., *Estrogen receptor beta in the breast: role in estrogen responsiveness and development of breast cancer*, J. Steroid Biochem Mol. Biol. (Nov. 2000) vol. 74, No. 5, pp. 245-248.

J.M. Hall et al., *Linkage of Early-Onset Familial Breast Cancer to Chromosome 17q21*, Science (Dec. 1990) vol. 250, No. 4988, pp. 1684-1689.

E. Haug et al., *Receptors for 17beta-estradiol in prolactin-secreting rat pituitary cells*, Mol. Cell Endocrinol (Oct. 1978) vol. 12, No. 1, pp. 81-95, PMID 569089 [PubMed—indexed for Medline], Abstract, http://www.ncbi.nlm.nih.gov/enrez/query.fcgi?cmd=Retrieve&db=PubMed&list_uids=569089&... printed on Feb. 19, 2003, 1 page.

I.C. Henderson et al., *The relationship between prognostic and predictive factors in the management of breast cancer*, Breast Cancer Res. Treat (1998) vol, 52, No. 1-3, pp. 261-288, PMID 10066087 [PubMed—indexed for Medline], Abstract, http://www.ncbi.nlm.nih.gov/enrez/query.fcgi?cmd=Retrieve&db=PubMed&list_uids=10066087&... printed on Feb. 21, 2003, 1 page.

J.S. Horoszewicz et al., *LNCaP model of human prostatic carcinoma*, Cancer Res. (Apr. 1983) vol. 43, No. 4, pp. 1809-1818.

K.B. Horwitz et al., *Steroid Receptor Analyses of Nine Human Breast Cancer Cell Lines*, Cancer Res. (Aug. 1978) vol. 38, No. 8, pp. 2434-2437.

M. Hosobuchi, *Effects of transforming growth factor beta on growth of human mammary epithelial cells in culture*, In Vitro Cell Dev Biol (Aug. 1989) vol. 24, No. 8, pp. 705-713, PMID 2548988 [PubMed—indexed for Medline], Abstract, http://www.ncbi.nlm.nih.gov/enrez/query.fcgi?cmd=Retrieve&db=PubMed&list_uids=2548988&... printed on Feb. 21, 2003, 1 page.

S. Jackson et al., *Normal human sera contain antibodies directed at Fab of IgA*, J Immunol (Apr. 1987) vol. 138, No. 7, pp. 2244-2248, PMID 3494062 [PubMed—indexed for Medline], Abstract, http://www.ncbi.nlm.nih.gov/enrez/query.fcgi?cmd=Retrieve&db=PubMed&list_uids=3494062&... printed on Feb. 21, 2003, 1 page.

N. Janin et al., *Breast cancer risk in ataxia telangiectasia (AT) heterozygotes: haplotype study in French AT families*, Br J Cancer (Jun. 1999) vol. 80, No. 7, pp. 1042-1045, PMID 10362113 [PubMed—indexed for Medline], Abstract, http://www.ncbi.nlm.nih.gov/enrez/query.fcgi?cmd=Retrieve&db=PubMed&list_uids=10362113&... printed on Feb. 21, 2003, 1 page.

E. Haug, *Progesterone suppression of estrogen-stimulated prolactin secretion and estrogen receptor levels in rat pituitary cells*, Endocrinology (Feb. 1979) vol. 104, No. 2, pp. 429-437, PMID 109280 [PubMed—indexed for Medline], Abstract, http://www.ncbi.nlm.nih.gov/enrez/query.fcgi?cmd=Retrieve&db=PubMed&list_uids=109280&... printed on Feb. 19, 2003, 1 page.

J. Gorski et al., *Hormone receptors: studies on the interaction of estrogen with the uterus*, Recent Prog Horm Res. (1968) vol. 24, pp. 45-80, PMID 4885833 [PubMed—indexed for Medline], Abstract, http://www.ncbi.nlm.nih.gov/enrez/query.fcgi?cmd=Retrieve&db=PubMed&list_uids=4885833&... printed on Feb. 20, 2003, 1 page.

K. el-Bayoumy, *Environmental carcinogens that may be involved in human breast cancer etiology*, Chem Res. Toxicol (Sep.-Oct. 1992) vol. 5, No. 5, pp. 585-590, PMID 1445997 [PubMed—indexed for Medline], Abstract, http://www.ncbi.nlm.nih.gov/enrez/query.fcgi?cmd=Retrieve&db=PubMed&list_uids=1445997&... printed on Feb. 21, 2003, 1 page.

D.F. Easton et al., *The genetic epidemiology of BRCAI. Breast Cancer Linkage Consortium*, Lancet (Sep. 1994) vol. 344, No. 8924, pp. 761, PMID 7915813 [PubMed—indexed for Medline], Abstract, http://www.ncbi.nlm.nih.gov/enrez/query.fcgi?cmd=Retrieve&db=PubMed&list_uids=7915813&... printed on Feb. 15, 2003, 1 page.

S.C. Brooks et al., *Estrogen receptor in a human cell line (MCF-7) from breast carcinoma*, J Biol Chem (Sep. 1973) vol. 248, No. 17, pp. 6251-6253, PMID 4353636 [PubMed—indexed for Medline], Abstract, http://www.ncbi.nlm.nih.gov/enrez/query.fcgi?cmd=Retrieve&db=PubMed&list_uids=4353636&... printed on Feb. 19, 2003, 1 page.

W.S. Bullough, *Chalone control mechanisms*, Life Sci (Feb. 1975) vol. 16, No. 3, pp. 323-330, PMID 12399 [PubMed—indexed for Medline], Abstract, http://www.ncbi.nlm.nih.gov/enrez/query.fcgi?cmd=Retrieve&db=PubMed&list_uids=123999&... printed on Feb. 12, 2003, 1 page.

E.V. Jensen et al., *A two-step mechanism for the interaction of estradiol with rat uterus*, Proc Natl. Acad. Sci USA (Feb. 1968) vol. 59, No. 2, pp. 632-638, PMID 5238991 [PubMed—indexed for Medline], Abstract, http://www.ncbi.nlm.nih.gov/enrez/query.fcgi?cmd=Retrieve&db=PubMed&list_uids=5238991&... printed on Feb. 20, 2003, 1 page.

E.V. Jensen et al., *Estrogen-receptor interaction*, Science (Oct. 1973) vol. 182, No. 108, pp. 126-134, PMID 4354173 [PubMed—indexed for Medline], Abstract, http://www.ncbi.nlm.nih.gov/enrez/query.fcgi?cmd=Retrieve&db=PubMed&list_uids=4354173&... printed on Feb. 20, 2003, 1 page.

F.E. Johansen et al., *Role of J Chain in Secretory Immunoglobulin Formation*, Scand. J. Immunol. (Sep. 2000) vol. 52, No. 3, pp. 240-248.

M.E. Kaighn et al., *Establishment and characterization of a human prostatic carcinoma cell line (PC-3)*, Invest. Urol. (Jul. 1979) No. 1, pp. 16-23, PMID 447482 [PubMed—indexed for Medline], Abstract, http://www.ncbi.nlm.nih.gov/enrez/query.fcgi?cmd=Retrieve&db=PubMed&list_uids=447482&... printed on Feb. 19, 2003, 1 page.

M. Kaufmann, *Review of known prognostic variables*, Recent Results Cancer Res. (1996) vol. 140, pp. 77-87, PMID 8787079 [PubMed—indexed for Medline], Abstract, http://www.ncbi.nlm.nih.gov/enrez/query.fcgi?cmd=Retrieve&db=PubMed&list_uids=8787079&... printed on Feb. 21, 2003, 1 page.

K.P. Karey et al., *Differential Responsiveness of Human Breast Cancer Cell Lines MCF-7 and T47D to Growth Factors and 17 Beta-Estradiol*, Cancer Res. (Jul. 1988) vol. 48, No. 14, pp. 4083-4092.

J.L. Kelsey et al., *Epidemiology of Breast Cancer*, Epidemiol Rev (1990), vol. 12, pp. 228-240.

R. Kemler et al., *In vitro studies on the selective binding of IgG from different species to tissue section s of the bovine mammary glands*, Eur J. Immunol (Sep. 1975) vol. 5, No. 9, pp. 603-608, PMID 11993319 [PubMed—indexed for Medline], Abstract, http://www.ncbi.nlm.nih.gov/enrez/query.fcgi?cmd=Retrieve&db=PubMed&list_uids=11993319&... printed on Feb. 15, 2003, 1 page.

N.J. Kenney et al., *Expression of Transforming Growth Factor Alpha Antisense mRNA Inhibits the Estrogen-Induced Production of TGF Alpha and Estrogen-Induced Proliferation of Estrogen-Responsive Human Breast Cancer Cells*, J. Cell Physiol (Sep. 1993) vol. 156, No. 3, pp. 497-514.

R.S. Kerbel et al., *Analysis of established human carcinoma cell lines for lynmphoreticular-associated membrane receptors*, Int. J. Cancer (Nov. 1977) vol. 20, No. 5, pp. 673-679, PMID 924690 [PubMed—indexed for Medline], Abstract, http://www.ncbi.nlm.nih.gov/enrez/query.fcgi?cmd=Retrieve&db=PubMed&list_uids=924690&... printed on Feb. 21, 2003, 1 page.

I. Keydar et al., *Establishment and characterization of a cell line of human breast carcinoma origin*, Eur J. Cancer (May 1979), vol. 15, No. 5, pp. 659-670.

M.S. Khan et al., *Size isomers of testosterone-estradiol-binding globulin exist in the plasma of individual men and women*, Steroids (May 1985), vol. 45, No. 5, pp. 463-472, PMID 3834662 [PubMed—indexed for Medline], Abstract, http://www.ncbi.nlm.nih.gov/enrez/query.fcgi?cmd=Retrieve&db=PubMed&list_uids=3834662&... printed on Feb. 21, 2003, 1 page.

K Kim et al., *Immunoglobulin G Subclasses in Human Colostrum, Milk and Saliva*, Acta Paediatr (Feb. 1992) vol. 81, No. 2, pp. 113-118, PMID 1515753 [PubMed—indexed for Medline], Abstract, http://www.ncbi.nlm.nih.gov/enrez/query.fcgi?cmd=Retrieve&db=PubMed&list_uids=1515753&... printed on Feb. 15, 2003, 1 page.

W.L. Kirkland et al., *Control of Cell Growth. III. Direct Mitogenic Effect of Thyroid Hormones on an Estrogen-Dependent Rat Pituitary Tumor Cell Line*, J. Natl. Cancer Inst. (Jun. 1976) vol. 56, No. 6 pp. 1159-1164.

C. Knabbe et al., *Evidence that transforming growth factor-beta is a hormonally regulated negative growth factor in human breast cancer cells*, Cell (Feb. 1987) vol. 48, No. 3, pp. 417-428, PMID 2879636 [PubMed—indexed for Medline], Abstract, http://www.ncbi.nlm.nih.gov/enrez/query.fcgi?cmd=Retrieve&db=PubMed&list_uids=2879636&... printed on Feb. 19, 2003, 1 page.

H. Kondoh et al., *Jacalin, a jackfruit lectin, precipitates IgA1 but not IgA2 subclass on gel diffusion reaction*, J. Immunol Methods (Apr. 1986) vol. 88, No. 2, pp. 171-173, PMID 3082992 [PubMed—indexed for Medline], Abstract, http://www.ncbi.nlm.nih.gov/enrez/query.fcgi?cmd=Retrieve&db=PubMed&list_uids=3082992&... printed on Feb. 21, 2003, 1 page.

H. Kubagawa et al., *A novel pair of immunoglobulin-like receptors expressed by B cells and myeloid cells*, Proc Natl. Acad. Sci USA (May 1997) vol. 94, No. 12, pp. 5993-5995.

M. Krainer et al., *Differential contributions of BRCA1 and BRCA2 to early-onset breast cancer*, N Engl J Med (May 1997) vol. 336, No. 20, pp. 1416-1421, (Original Articles) 12 pages.

P. Krajci et al., *Molecular cloning and exon-intron mapping of the gene encoding human transmembrance secretory component (the poly-Ig receptor)*, Eur J Immunol (Sep. 1992) vol. 22, No. 9, pp. 2309-2315.

P. Krajci et al., *Secretory component mRNA and protein expression of colorectal adenomas an carcinomas*, Br J Cancer (Jun. 1996) vol. 73, No. 12, pp. 1503-1510.

P. Krajci et al., *The gene encoding human transmembrane secretory component (locus PIGR) is linked to DIS58 on chromosome 1*, Hum Genet (Nov. 1992) vol. 90, No. 3, pp. 215-219, PMID 1487233 [PubMed—indexed for Medline], Abstract, http://www.ncbi.nlm.nih.gov/enrez/query.fcgi?cmd=Retrieve&db=PubMed&list_uids=1487233&... printed on Feb. 21, 2003, 1 page.

P. Krajci et al., *The human transmembrane secretory component (poly-Ig receptor): molecular cloning, restriction fragment length polymorphism and chromosomal sublocalization*, Hum Genet (Oct. 1991) vol. 87, No. 6, pp. 642-648.

P. Krajci et al., *Cloning, chromosomal localization, and linkage analysis of the gene encoding human transmembrane secretory component (the poly-Ig receptor)*, Adv Exp. Med Biol (1995) No. 371A, pp. 617-623, PMID 8526003 [PubMed—indexed for Medline], Abstract, http://www.ncbi.nlm.nih.gov/enrez/query.fcgi?cmd=Retrieve&db=PubMed&list_uids=8526003&... printed on Feb. 21, 2003, 1 page.

G.G. Kuiper et al., *Cloning of a novel receptor expressed in rat prostate and ovary*, Proc Natl. Acad. Sci USA (Jun. 1996) vol. 93, No. 12, pp. 5925-5930.

G.G. Kuiper et al., *Interaction of estrogen chemicals and phytoestrogens with estrogen receptor beta*, Endocrinology (Oct. 1998) vol. 139, No. 10, pp. 4252-4263.

G.G. Kuiper et al., *Comparison of the ligand binding specificity and transcript tissue distribution of estrogen receptors alpha and beta*, Endocrinology (Mar. 1997) vol. 138, No. 3, pp. 863-870.

R. Kumar et al., *The structure of nuclear hormone receptors*, Steroids (May 1999) vol. 64, No. 5, pp. 310-319.

I. Laursen et al., *Serum albumin as a modulator on growth of the human breast cancer cell line, MCF-7*, Anticancer Res. (Mar.-Apr. 1990) vol. 10, No. 2A, pp. 343-351, PMID 2346307 [PubMed—indexed for Medline], Abstract, http://www.ncbi.nlm.nih.gov/enrez/query.fcgi?cmd=Retrieve&db=PubMed&list_uids=2346307&... printed on Feb. 12, 2003, 1 page.

P. Lemieux et al., *The Role of the Estrogen Receptor in Tumor Progression*, J. Steroid Biochem Mol Biol (Jan. 1996), vol. 56, Nos. 1-6, pp. 87-91.

J.J. Letterio et al., *Regulation of Immune Responses by TGF-beta*, Annu Rev Immunol, No. 16, pp. 137-161.

C. Lengauer et al., *Genetic instability in colorectal cancers*, Nature (Apr. 1997), vol. 386, No. 6625, pp. 623-627 [Letter] 10 pages.

L.M. Loomes et al., *Purification and characterization of human immunoglobulin IgA1 and IgA2 isotypes from serum*, J Immunol Methods (Aug. 1991) vol. 141, No. 2, pp. 209-218, PMID 1880427

[PubMed—indexed for Medline], Abstract, http://www.ncbi.nlm.nih.gov/enrez/query.fcgi?cmd=Retrieve&db=PubMed&list_uids=1880427&... printed on Feb. 21, 2003, 1 page.

M.L. Loupart et al., *Allelic imbalance on chromosome I in human breast cancer. I. Minisatellite and RFLP analysis*, Genes Chromosomes Cancer (Jan. 1995) vol. 12, No. 1, pp. 16-23, PMID 7534106 [PubMed—indexed for Medline], Abstract, http://www.ncbi.nlm.nih.gov/enrez/query.fcgi?cmd=Retrieve&db=PubMed&list_uids=7534106&... printed on Feb. 21, 2003, 1 page.

E. Lullau et al., *Antigen Binding Properties of Purified Immunoglobulin A and Reconstituted Secretory Immunoglobulin A Antibodies*, J Biol Chem (Jul. 1996) vol. 271, No. 27, pp. 16300-0.

S. Mathew et al., *Transforming growth factor receptor gene TGFBR2 maps to human chromosome band 3p22*, Genomics (Mar. 1994) vol. 20, No. 1, pp. 114-115, PMID 8020936 [PubMed—indexed for Medline], Abstract, http://www.ncbi.nlm.nih.gov/enrez/query.fcgi?cmd=Retrieve&db=PubMed&list_uids=8020936&... printed on Feb. 21, 2003, 1 page.

M.I. McBurney et al., *Colonic carcinogenesis: the microbial feast or famine mechanism*, Nutr Cancer (1987) vol. 10, No. 1-2, pp. 23-28, PMID 3039469 [PubMed—indexed for Medline], Abstract, http://www.ncbi.nlm.nih.gov/enrez/query.fcgi?cmd=Retrieve&db=PubMed&list_uids=3039469&... printed on Feb. 15, 2003, 1 page.

J. Mestecky et al., *Immunoglobulin A (IgA): Molecular and Cellular Interactions Involved in IgA Biosynthesis and Immune Response*, Adv Immunol (1987) vol. 40, pp. 153-245.

J. Mestecky et al., *Evaluation of monoclonal antibodies with specificity for human IgA, IgA subclasses and allotypes and secretory component. Results of an IUIS/WHO collaborative study*, J Immunol Methods (Jun. 1996), vol. 193, No. 2, pp. 103-148.

J.E. Moreno-Cuevas et al., *Estrogen mitogenic action. III. Is phenol red a "red herring"?*, In Vitro Cell Dev Biol Anim (Jul.-Aug. 2000) vol. 36, No. 7, pp. 447-464.

W.L. McKeehan et al., *Frontiers in Mammalian Cell Culture*, in Vitro Cell Dev Biol (Jan. 1990) vol. 26, No. 1, pp. 9-23.

S. Mosselman et al., *ER beta: identification and characterization of a novel human estrogen receptor*, FEBS Lett (Aug. 1996) vol. 392, No. 1, pp. 49-53, PMID 8769313 [PubMed—indexed for Medline], Abstract, http://www.ncbi.nlm.nih.gov/enrez/query.fcgi?cmd=Retrieve&db=PubMed&list_uids=8769313&... printed on Feb. 19, 2003, 1 page.

L.C. Murphy et al., *Variant estrogen receptor mRNA species detected in human breast cancer biopsy sample*, Mol Endocrinol (Apr. 1989) vol. 3, No. 4, pp. 687-693, PMID 2725532 [PubMed—indexed for Medline], Abstract, http://www.ncbi.nlm.nih.gov/enrez/query.fcgi?cmd=Retrieve&db=PubMed&list_uids=2725532&... printed on Feb. 20, 2003, 1 page.

A.M. Nakhla et al., *Induction of adenylate cyclase in a mammary carcinoma cell line by human corticosteroid-binding globulin*, Biochem Biophys Res. Commun (Jun. 1988) vol. 153, No. 3, pp. 1012-1018, PMID 2839166 [PubMed—indexed for Medline], Abstract, http://www.ncbi.nlm.nih.gov/enrez/query.fcgi?cmd=Retrieve&db=PubMed&list_uids=2839166&... printed on Feb. 19, 2003, 1 page.

A.M. Nakhla et al., *Characterization of ALVA-41 cells, a new human prostatic cancer cell line*, Steroids (Oct. 1994) vol. 10, pp. 586-589.

K.A. Nathavitharana et al., *Presence of secretory IgA antibodies to an enteric bacterial pathogen in human milk and saliva*, Arch Dis Child Fetal Neonatal Ed (Mar. 1995) vol. 72, No. 2, pp. F102-F106, (Original Article) 8 pages.

J.R. Nevens et al., *Affinity Chromatographic Purification of Immunoglobulin M Antibodies Utilizing Immobilized Mannan Binding Protein*, J Chromatogr (Apr. 1992) vol. 597, Nos. 1-2, pp. 247-256.

F.R. Ochsendorf, *Infections in the male genital tract and reactive oxygen species*, Hum Reprod Update (Sep.-Oct. 1999) vol. 5, No. 5, pp. 399-420, PMID 10582780 [PubMed—indexed for Medline], Abstract, http://www.ncbi.nlm.nih.gov/enrez/query.fcgi?cmd=Retrieve&db=PubMed&list_uids=10582780&... printed on Feb. 22, 2003, 1 page.

M. Ogasawara et al., *A new serum-free method of measuring growth factor activities for human breast cancer cells in culture*, in Vitro Cell Dev Biol (Sep. 1988) vol. 24, No. 9, pp. 911-920.

J.H. Olsen et al., *Cancer in Patients With Ataxia-Telangiectasia and in Their Relatives in the Nordic Countries*, J Natl. Cancer Inst. (Jan. 2001) vol. 93, No. 2, pp. 121-127.

B.W. O'Malley et al., *Female steroid hormones and target cell nuclei*, Science (Feb. 1974) vol. 183, No. 125, pp. 610-620, PMID 4359082 [PubMed—indexed for Medline], Abstract, http://www.ncbi.nlm.nih.gov/enrez/query.fcgi?cmd=Retrieve&db=PubMed&list_uids=4359082&... printed on Feb. 20, 2003, 1 page.

C.K. Osborne, *Steroid hormone receptors in breast cancer management*, Breast Cancer Res. Treat (1998) vol. 51, No. 3, pp. 227-238, PMID 10068081 [PubMed—indexed for Medline], Abstract, http://www.ncbi.nlm.nih.gov/enrez/query.fcgi?cmd=Retrieve&db=PubMed&list_uids=10068081&...printed on Feb. 21, 2003, 2 pages.

T.D. Pack, *Bacterial binding protein for single-step purification of human IgA*, Application Note (Apr. 1999), pp. 16, 18.

M.A. Palladino et al., *The transforming growth factor-betas. A new family of immunoregulatory molecules*, Ann NY Acad. Sci (1990) vol. 593, pp. 181-187, PMID 2197960 [PubMed—indexed for Medline], Abstract, http://www.ncbi.nlm.nih.gov/enrez/query.fcgi?cmd=Retrieve&db=PubMed&list_uids=2197960&... printed on Feb. 12, 2003, 1 page.

B. Peitersen et al., *Quantitative Determination of Immunoglobulins, lysozyme, and Certain Electrolytes in breast Milk During the Entire Period of Lactation, During a 24-hour Period, and in Milk from the Individual Mammary Gland*, Acta Paediatr Scand (Sep. 1975), vol. 64, No. 5, pp. 709-717.

U. Pfeffer et al., *Estrogen receptor variant messenger RNA lacking exon 4 in estrogen-responsive human breast cancer cell lines*, Cancer Res. (Feb. 1993) vol. 53, No. 4, pp. 741-743, PMID 7916651 [PubMed—indexed for Medline], Abstract, http://www.ncbi.nlm.nih.gov/enrez/query.fcgi?cmd=Retrieve&db=PubMed&list_uids=7916651&... printed on Feb. 20, 2003, 1 page.

M. Raghavan et al., *Fc Receptors and Their Interactions With Immunoglobulins*, Annu. Rev. Cell Dev. Biol. (1996) vol. 12, pp. 181-220.

R.R. Reddel et al., *Differential Sensitivity of Human Breast Cancer cell Lines to the Growth-Inhibitory Effects of Tamoxifen*, Cancer Res. (Apr. 1985) vol. 45, No. 4, pp. 1525-1531.

C.C. Reese et al., *Alternative models for estrogen and androgen regulation of human breast cancer cell (T47D) growth*, Ann NY Acad. Sci (1988) vol. 538, pp. 112-121, PMID 3190080 [PubMed—indexed for Medline], Abstract, http://www.ncbi.nlm.nih.gov/enrez/query.fcgi?cmd=Retrieve&db=PubMed&list_uids=3190080&... printed on Feb. 12, 2003, 1 page.

I. Laursen et al., *Serum Albumin as a Modulator on Growth of the Human Breast Cancer Cell Line, MCF-7*, Anticancer Research (1990) vol. 10, pp. 343-352.

C.B. Reimer et al., *Specificity and association constants of 33 monoclonal antibodies to human IgA epitopes*, Immunol Lett (Jun. 1989) vol. 21, No. 3, pp. 209-215, PMID 2475439 [PubMed—indexed for Medline], Abstract, http://www.ncbi.nlm.nih.gov/enrez/query.fcgi?cmd=Retrieve&db=PubMed&list_uids=2475439&... printed on Feb. 22, 2003, 1 page.

M. Reiss et al., *Transforming growth factor-beta in breast cancer: a working hypothesis*, Breast Cancer Res. Treat (Aug. 1997) vol. 45, No. 1, pp. 81-95, PMID 9285120 [PubMed—indexed for Medline], Abstract, http://www.ncbi.nlm.nih.gov/enrez/query.fcgi?cmd=Retrieve&db=PubMed&list_uids=9285120&... printed on Feb. 21, 2003, 1 page.

J.M. Renoir et al., *Hormonal and immunological aspects of the phylogeny of sex steroid binding plasma protein*, Proc Natl. Acad. Sci USA (Aug. 1980) Vol. 77, No. 8, pp. 4578-4582.

J.L. Reny et al., *Human Serum Does Not Contain a High Affinity Estrogen-Binding Glycoprotein Different From Sex Hormone-Binding Globulin*, J Clin Endocrinol Metab (May 1989) vol. 68, No. 5, pp. 938-945.

S.F. Retia et al., *Purification of fibronectin from human plasma*, Methods Mol Biol (1999) vol. 96, pp. 119-124, PMID 10098128 [PubMed—indexed for Medline], Abstract, http://www.ncbi.nlm.

nih.gov/enrez/query.fcgi?cmd=Retrieve&db=PubMed&list_uids=10098128&... printed on Mar. 12, 2003, 1 page.

A. Richardson, *Is breast cancer caused by late exposure to a common virus?* Med Hypotheses (Jun. 1997) vol. 48, No. 6, pp. 491-497, PMID 9247892 [PubMed—indexed for Medline], Abstract, http://www.ncbi.nlm.nih.gov/enrez/query.fcgi?cmd=Retrieve&db=PubMed&list_uids=9247892&... printed on Feb. 22, 2003, 1 page.

T.L. Riss et al., *Rat Pituitary Tumor Cells in Serum-Free Culture. II. Serum Factor and Thyroid Hormone Requirements for Estrogen-Responsive Growth*, In Vitro Cell Dev Biol. (Feb. 1989) vol. 25, No. 2, pp. 136-142.

T.L. Riss et al., *Purification and Identification of Transferrin as a Major Pituitary-Derived Mitogen for MTW9/PL2 Rat Mammary Tumor Cells*, in Vitro Cell Dev Biol (Dec. 1987) vol. 23, No. 12, pp. 841-849.

T.L. Riss et al., *Rat Pituitary Tumor Cells in Serum-Free Culture. I. Selection of Thyroid Hormone-Responsive and Autonomous Cells*, in Vitro Cell Dev Biol (Feb. 1989) vol. 25, No. 2, pp. 127-135.

T.L. Riss et al., *Growth and Continuous Passage of COMMA-D Mouse Mammary Epithelial Cells in Hormonally Defined Serum-Free Medium*, Cancer Res. (Jul. 1987) vol. 47, No. 14, pp. 3776-3782.

T.L. Riss et al., *Human Recombinant Insulin-Like Growth Factor I. I. Development of a Serum-Free Medium for Clonal Density Assay of Growth Factors Using BALB/c 3T3 Mouse Embryo Fibroblasts*, In Vitro Cell Dev Biol (Nov. 1988) vol. 24, No. 11, pp. 1099-1106.

M.C. Roque-Barreira et al., *Jacalin: an IgA-binding lectin*, J Immunol (Mar. 1985) vol. 134, No. 3, pp. 1740-1743, PMID 3871459 [PubMed—indexed for Medline], Abstract, http://www.ncbi.nlm.nih.gov/enrez/query.fcgi?cmd=Retrieve&db=PubMed&list_uids=3871459&... printed on Feb. 21, 2003, 1 page.

M.C. Roque-Barreira et al., *IgA-affinity purification and characterization of the lectin jacalin*, Braz J Med Biol Res. (1986) vol. 19, No. 2, pp. 149-157.

W. Rosner et al., *Isolation and Characterization of the Testosterone-Estradiol-Binding Globulin From Human Plasma. Use of a Novel Affinity Column*, Biochemistry (Nov. 1975) vol. 14, No. 22, pp. 4813-4820.

W. Rosner, *The Functions of Corticosteroid-Binding Globulin and Sex Hormone-Binding Globulin: Recent Advances*, Endocr Rev (Feb. 1990) vol. 11, No. 1, pp. 80-91.

W. Rosner et al., *Testosterone-Estradiol-Binding Globulin of Human Plasma: Denaturation and Protection*, Biochim Biophys Acta (May 1974) vol. 351, No. 1, pp. 92-98.

J. Russo et al., *DNA Labeling Index and Structure of the Rat Mammary Gland as Determinants of its Susceptibility to Carcinogenesis*, J Natl. Cancer Inst. (Dec. 1978), vol. 61, No. 6, pp. 14511459.

I.H. Russo et al., *Developmental Stage of the Rat Mammary Gland as Determinant of its Susceptibility to 7,12-Dimethylbenz(a)anthracene*, J Natl. Cancer Inst. (Dec. 1978) vol. 61, No. 6, pp. 1439-1449.

M. Sabel et al., *Recent developments in breast imagining*, Phys Med Biol (Mar. 1996), vol. 41, No. 3, pp. 315-368, PMID 8778818 [PubMed—indexed for Medline], Abstract, http://www.ncbi.nlm.nih.gov/enrez/query.fcgi?cmd=Retrieve&db=PubMed&list_uids=8778818&... printed on Feb. 21, 2003, 1 page.

R. Sager, *Expression genetics in cancer: shifting the focus from DNA to RNA*, Proc Natl. Acad. Sci USA (Feb. 1997), vol. 94, No. 3, pp. 952-959.

H.H. Samuels et al., *Depletion of L-3,5,3'-Triiodothyronine and L-Thyroxine in Euthyroid Calf Serum for Use in Cell Culture Studies of the Action of Thyroid Hormone*, Endocrinology (Jul. 1979) vol. 105, No. 1, pp. 80-85.

H. Sato et al., *Iron is deleterious to hormone-responsive pituitary cell growth in serum-free defined medium*, In Vitro Cell Dev Biol (Aug. 1991), vol. 27A, No. 8, pp. 599-602.

H. Sato et al., *Apotransferrins from several species promote thyroid hormone-dependent rat pituitary tumor cell growth in iron-restricted serum-free defined culture*, Mol Cell Endocrinol (Feb. 1992), vol. 83, Nos. 2-3, pp. 239-251.

R.W. Schatz et al., *Effects of Interaction Between Estradiol-17 Beta and Progesterone on the Proliferation of Cloned Breast Tumor Cells (MCF-7 and T47D)*, J Cell Physiol (Sep. 1985) vol. 124, No. 3, pp. 386-390.

A. Segaloff, *Hormone Therapy of Breast Cancer*, Banbury Report; 8 (1981), pp. 229-236.

J. Seidenfeld et al., *Single-Therapy Androgen Suppression in Men With Advanced Prostate Cancer: A Systematic Review and Meta-Analysis*, Ann Intern Med (Apr. 2000) vol. 132, No. 7, pp. 566-577.

G.B. Silberstein et al., *Regulation of Mammary Morphogenesis: Evidence for Extracellular Matrix-Mediated Inhibition of Ductal Budding by Transforming Growth Factor-Beta 1*, Dev Biol (Aug. 1992), vol. 152, No. 2, pp. 354-362.

G.B. Silberstein et al., *Reversible Inhibition of Mammary Gland Growth by Transforming Growth Factor-Beta*, Science (Jul. 1987) vol. 237, No. 4812, pp. 291-293.

D.A. Sirbasku, *Hormone-Responsive Growth in Vivo of a Tissue Culture Cell Line Established From the MT-W9A Rat Mammary Tumor*, Cancer Res. (Apr. 1978) vol. 38, No. 4, pp. 1154-1165.

D.A. Sirbasku et al., *Thyroid Hormone and Apotransferrin Regulation of Growth Hormone Secretion by GHI Rat Pituitary Tumor Cells in Iron Restricted Serum-Free Defined Medium*, In Vitro Cell Dev Biol (Jan. 1992), vol. 28A, No. 1, pp. 67-71.

D.A. Sirbasku et al., *Thyroid Hormone Regulation of Rat Pituitary Tumor Cell Growth: A New Role for Apotransferrin As an Autocrine Thyromedin*, Mol Cell Endocrinol (May 1991) vol. 77, Nos. 1-3, pp. C47-C55.

D.A. Sirbasku et al., *Purification of an Equine Apotransferrin Variant (Thyromedin) Essential for Thyroid Hormone Dependent Growth of GHI Rat Pituitary Tumor Cells in Chemically Defined Culture*, Biochemistry (Jan. 1991) vol. 30, No. 1, pp. 295-304.

D.A. Sirbasku et al., *Control of Cell Growth. IV. Growth Properties of a New Cell Line Established Front an Estrogen-Dependent Kidney Tumor of the Syrian Hamster*. Endocrinology (May 1976) vol. 98, No. 5, pp. 1260-1272.

D.A. Sirbasku et al., *Thyroid Hormone Dependent Pituitary Tumor Cell Growth in Serum-Free Chemically Defined Culture. A New Regulatory Role for Apotransferrin*, Biochemistry (Jul. 1991) vol. 30, No. 30, pp. 7466-7477.

D.A. Sirbasku et al., *Survey of the Mechanisms Regulating Estrogen Promoted Breast Cancer Cell Growth*, DOD Breast Cancer Research (Jun. 2000) Era of Hope, Proceedings vol. II, 2 pages.

D.A. Sirbasku, *Estrogen induction of growth factors specific for hormone-responsive mammary, pituitary, and kidney tumor cells*, Proc Natl. Acad. Sci USA (Aug. 1978) vol. 75, No. 8, pp. 3786-3790.

D.A. Sirbasku et al., *Estrogen mitogenic action. Ii. Negative regulation of the steroid hormone-responsive growth of cell lines derived from human and rodent target tissue tumors and conceptual implications*, In Vitro Cell Dev Biol Anim (Jul.-Aug. 2000) vol. 36, No. 7, pp. 428-446.

D.A. Sirbasku, *New Concepts in Control of Estrogen-Responsive Tumor Growth*, Banbury Report; 8 (1981), pp. 405-443.

E.P. Smith et al., *Estrogen Resistance Caused by a Mutation in the Estrogen-Receptor Gene in a Man*, N. Engl J Med (Oct. 1994) vol. 331, No. 16, pp. 1056-1061.

R.L. Smith et al., *Separation of plasma fibronectin from associated hemagglutinating acivity by elution from gelatin-agarose at pH 5.5*, Thromb Res. (Jan. 1985), vol. 37, No. 1, pp. 91-101, PMID 3983905 [PubMed—indexed for Medline], Abstract, http://www.ncbi.nlm.nih.gov/enrez/query.fcgi?cmd=Retrieve&db=PubMed&list_uids=3983905&... printed on Feb. 20, 2003, 1 page.

M.J. Smyth et al., *A fresh look at tumor immunosurveillance and immunotherapy*, Nat Immunol (Apr. 2001) vol. 2, No. 4, pp. 293-299.

C. Sonneschein et al., *Somatic Mutation Theory of Carcinogenesis: Why It Should Be Dropped and Replaced*, Molecular Carcinogenesis (Dec. 2000) vol. 29, No. 4, pp. 205-211.

C. Sonneschein et al., *Human Serum Albumin Shares the Properties of Estrocolyone-1, The Inhibitor of the Proliferation of Estrogen-Target Cells*, J Steroid Biochem Mol Biol (Oct. 1996) vol. 59, No. 2, pp. 147-154.

A.M. Soto et al., *Cell proliferation of estrogen-sensitive cells: the case for negative control*, Endoc Rev (Feb. 1987), vol. 8, No. 1, pp. 44-52.

A.M. Soto et al., *The role of estrogens on the proliferation of human breast tumor cells*, J Steroid Biochem (Jul. 1985) vol. 23, No. 1, pp. 87-94, PMID 4021494 [PubMed—indexed for Medline], Abstract, http://www.ncbi.nlm.nih.gov/enrez/query.fcgi?cmd=Retrieve&db=PubMed&list_uids=4021494&... printed on Feb. 20, 2003, 1 page.

A.M. Soto et al., *Estrogen-Sensitive Proliferation pattern of Cloned Syrian Hamster Kidney Tumor Cells*, Cancer Res. (Jul. 1988), vol. 48, No. 13, pp. 3676-3680, PMID 3288332 [PubMed—indexed for Medline], Abstract, http://www.ncbi.nlm.nih.gov/enrez/query.fcgi?cmd=Retrieve&db=PubMed&list_uids=3288332&... printed on Feb. 20, 2003, 1 page.

A.M. Soto et al., *Control of Cell Proliferation: Evidence for Negative Control on Estrogen-Sensitive T47D Human Breast Cancer Cells*, Cancer Res. (May 1986) vol. 46, No. 5, pp. 2271-2275.

A.M. Soto et al., *A Plasma-Borne Specific Inhibitor of the Proliferation of Human Estrogen-Sensitive Breast Tumor Cells (Estrocolyone-I)*, J. Steroid Biochem Mol Biol (Dec. 1992) vol. 43, No. 7, pp. 703-712.

H.D. Soule et al., *A human cell line from apleural effusion derived from a breast carcinoma*, J Natl. Cancer Inst. (Nov. 1973) vol. 51, No. 5, pp. 409-416, PMID 4357757 [PubMed—indexed for Medline], Abstract, http://www.ncbi.nlm.nih.gov/enrez/query.fcgi?cmd=Retrieve&db=PubMed&list_uids=4357757&... printed on Feb. 19, 2003, 1 page.

H.L. Spiegelberg, *Biological activities of immunoglobulins of different classes and subclasses*, Adv Immunol (1974) vol. 19, pp. 259-294, PMID 4611172 [PubMed—indexed for Medline], Abstract, http://www.ncbi.nlm.nih.gov/enrez/query.fcgi?cmd=Retrieve&db=PubMed&list_uids=4611172&... printed on Feb. 15, 2003, 1 page.

J.E. Stern et al., *Secretory immune system of the male reproductive tract: effects of dihydrotestosterone and estradiol on IgA and secretory component levels*, J Reprod Immunol (Jun. 1992) vol. 22, No. 1, pp. 73-85, PMID 1522564 [PubMed—indexed for Medline], Abstract, http://www.ncbi.nlm.nih.gov/enrez/query.fcgi?cmd=Retrieve&db=PubMed&list_uids=1522564&... printed on Feb. 22, 2003, 1 page.

J.E. Stern et al., *Secretory component in breast cancer. Analysis of the levels in primary and metastatic disease*, Cancer Immunol. Immunother. (1985) vol. 19, No. 2, pp. 226-230, PMID 3847292 [PubMed—indexed for Medline], Abstract, http://www.ncbi.nlm.nih.gov/enrez/query.fcgi?cmd=Retrieve&db=PubMed&list_uids=3847292&... printed on Feb. 21, 2003, 1 page.

K.R. Stone et al., *Isolation of a Human Prostate Carcinoma Cell Line (DU 145)*, Int. J. Cancer (Mar. 1978), vol. 21, No. 3, pp. 274-281.

J.S. Strobl et al., *Prolonged Retention of Estadiol by Human Breast Cancer Cells in Tissue Culture*, Cancer Res. (Sep. 1979) vol. 39, No. 9, pp. 3319-3327.

R.L. Sutherland et al., *High-Affinity Anti-Oestrogen Binding Site Distinct From the Oestrogen Receptor*, Nature (Nov. 1980) vol. 288, No. 5788, pp. 273-275, PMID 7432524 [PubMed—indexed for Medline], Abstract, http://www.ncbi.nlm.nih.gov/enrez/query.fcgi?cmd=Retrieve&db=PubMed&list_uids=7432524&... printed on Feb. 20, 2003, 1 page.

M. Swift, *Public health Burden of Cancer in Ataxia-Telangiectasia Heterozygotes*, J. Natl. Cancer Inst. (Jan. 2001), vol. 92, No. 2, pp. 84-85.

M. Tanji et al., *A Steroid-Binding Protein Mediates Estrogen-Dependent Inhibition of Growth of MCF-7 Breast Cancer Cells*, Anticancer Res. (Jul.-Aug. 2000) vol. 20, No. 4, pp. 2785-2789.

M. Tanji et al., *Growth Inhibition of MCF-7 Cells by Estrogen Is Dependent Upon a Serum Factor*, Anticancer Res. (Jul.-Aug. 2000) vol. 20, No. 4, pp. 2779-2783.

A.H. Tashjian, *Clonal Strains of Hormone-Producing Pituitary Cells*, Methods Enymol (1979) vol. 58, pp. 527-535.

S.V. Tavtigian et al., *The Complete BRCA2 Gene and Mutations in Chromosome 13q-Linked Kindreds*, Nat. Genet (Mar. 1996) vol. 12, No. 3, pp. 333-337, PMID 8589730 [PubMed—indexed for Medline], Abstract, http://www.ncbi.nlm.nih.gov/enrez/query.fcgi?cmd=Retrieve&db=PubMed&list_uids=8589730&... printed on Feb. 15, 2003, 1 page.

M.J. Tsai et al., *Molecular mechanisms of action of steroid/thyroid receptor superfamily members*, Annu. Rev. Biochem (1994) vol. 63, pp. 451-486, PMID 7979245 [PubMed—indexed for Medline], Abstract, http://www.ncbi.nlm.nih.gov/enrez/query.fcgi?cmd=Retrieve&db=PubMed&list_uids=7979245&... printed on Feb. 21, 2003, 1 page.

J.P. Vaerman et al., *Antibody against the human J chain inhibits polymeric Ig receptor-medicated biliary and epithelial transport of human polymeric IgA*, Eur. J. Immunol. (Jan. 1998) vol. 28, pp. 171-182.

S. Valtanen et al., *Poliovirus-Specific Intestinal Antibody Responses Coincide With Decline of Poliovirus Excretion*, J. Infect. Dis. (Jul. 2000) vol. 182, pp. 1-5.

J. Veldscholte et al., *A mutation in the ligand binding domain of the androgen receptor of human LNCaP cells affects steroid binding characteristics and response to anti-androgens*, Biochem Biophys Res. Commun (Dec. 1990) vol. 173, No. 2, pp. 534-540.

J. Veldscholte et al., *Unusual specificity of the androgen receptor in the human prostate tumor cell line LNCaP: high affinity for progestagenic and estrogenic steroids*, Biochim Biophys Acta (Apr. 1990) vol. 105, pp. 187-194.

F. Vignon et al., *Effects of Plasma Estrogen Sulfates in Mammary Cancer Cells*, Endocrinology (Apr. 1980) vol. 106, No. 4, pp. 1079-1086.

F. Vignon et al., *Antiestrogens inhibit the mitogenic effect of growth factors on breast cancer cells in the total absence of estrogens*, Biochem Biophys Res. Commun (Aug. 1987) vol. 146, No. 3, pp. 1502-1508, PMID 3304294 [PubMed—indexed for MEDLINE], Abstract, http://www.ncbi.nlm.nih.gov/enrez/query.fcgi?cmd=Retrieve&db=PubMed&list_uids=&3304294... printed on Feb. 20, 2003, 1 page.

J.F. Viret et al., *Mucosal and systemic immune responses in humans after primary and booster immunizations with orally administered invasive and noninvasive live attenuated bacteria*, Infect Immun (Jul. 1999) vol. 67, No. 7, pp. 3680-3685.

I Vorechovsky et al., *the ATM gene and susceptibility to breast cancer: analysis of 38 breast tumors reveals no evidence for mutation*, Cancer Res. (Jun. 1996) vol. 56, No. 12, pp. 2726-2732, PMID 8665503 [PubMed—indexed for Medline], Abstract, http://www.ncbi.nlm.nih.gov/enrez/query.fcgi?cmd=Retrieve&db=PubMed&list_uids=8665503&... printed on Feb. 21, 2003, 1 page.

Y. Wang et al., *Identification of a dominant negative form of the human estrogen receptor*, Mol. Endocrinol (Nov. 1991) vol. 5, No. 11, pp. 1707-1715, PMID 1779972 [PubMed—indexed for Medline], Abstract, http://www.ncbi.nlm.nih.gov/enrez/query.fcgi?cmd=Retrieve&db=PubMed&list_uids=1779972&... printed on Feb. 20, 2003, 1 page.

C.W. Welsch, *Host Factors Affecting the Growth of Carcinogen-induced Rat Mammary Carcinomas: A Review and Tribute to Charles Brenton Huggin*, Cancer Res. (Aug. 1985) vol. 45, No. 8, pp. 3415-3443.

R.V. Wenn et al., *Distribution of Testosterone-Estradiol Binding Globulin (TeBG) in the Higher Vertebrates*, Endokrinologie (Jul. 1977) vol. 69, No. 2, pp. 151-156.

T.E. Wiese et al., *Optimization of estrogen growth response in MCF-7 cells*, in Vitro Cell Dev Biol (Sep.-Oct. 1992) vol. 28A, No. 9-10, pp. 595-602.

R. Wooster et al., *Identification of the breast cancer susceptibility gene BRCA2*, Nature (Dec. 1995) vol. 378, No. 6559, pp. 789-792, PMID 8524414 [PubMed—indexed for Medline], Abstract, http://www.ncbi.nlm.nih.gov/enrez/query.fcgi?cmd=Retrieve&db=PubMed&list_uids=8524414&... printed on Feb. 15, 2003, 1 page.

J. Yang et al., *Estrogen receptor variants in epithelial compartment of normal human breast*, Endocrine (Jun. 2000), vol. 12, No. 3, pp. 243-247, PMID 10963044 [PubMed—indexed for Medline], Abstract, http://www.ncbi.nlm.nih.gov/enrez/query.fcgi?cmd=Retrieve&db=PubMed&list_uids=10963044&... printed on Feb. 12, 2003, 1 page.

K.R. Yamamoto, *Steroid receptor regulated transcription of specific genes and gene networks*, Annu Rev Genet (1985) vol. 19, pp. 209-252, PMID 3909942 [PubMed—indexed for Medline], Abstract, http://www.ncbi.nlm.nih.gov/enrez/query.fcgi?cmd=Retrieve&db=PubMed&list_uids=3909942&... printed on Feb. 21, 2003, 1 page.

D.A. Zajchowski et al., *Estrogen inhibits the growth of estrogen receptor-negative, but not estrogen receptor-positive, human mammary epithelial cells expressing a recombination estrogen receptor*, Cancer Res. (Oct. 1993) vol. 53, No. 20, pp. 5004-5011, PMID 8402691 [PubMed—indexed for Medline], Abstract, http://www.ncbi.nlm.nih.gov/enrez/query.fcgi?cmd=Retrieve&db=PubMed&list_uids=8402691&... printed on Feb. 21, 2003, 1 page.

International Search Report, PCT/US02/36632 dated Jul. 28, 2003 (1 p.).

Brodie et al. Aromatase inhibitors and their antitumor effects in model systems, Anticancer Research, Jun. 1999, vol. 6, No. 2, pp. 205-210.

McCormick et al., Exceptional Chemopreventive activity of low-dose dehydroepiandrosterone in the rat mammary gland, Cancer Research, vol. 56, No. 8, 1996, pp. 1724-1726.

Rosso et al. Adjuvant Systemic Treatment of Resectable Breast Cancer Eleven Years Results of a Monoinstutitional Chemo-Hormone-Immunotherapy Trial, Anticancer Research, vol. 9, No. 4, 1989, pp. 1153-1156.

Savage et al., A phase I clinical trial of imiquimod, an oral interferon inducer, administered daily, British Journal of Cancer, vol. 71, No. 9, 1996, pp. 1482-1486.

Sawai et al., Chemo-Endocrine-Immunotherapy With Adriamycin Tamoxifen and OK-432 Picibanil for Advanced Breast Cancer, Journal of Japan Society for Cancer Therapy, vol. 19, No. 6, 1984, pp. 1315-1320.

Supplemental European Search Report dated Feb. 14, 2006.

Furuya et al (Cancer Research, Dec. 1989, vol. 49, pp. 6670-6674).

Hoffman ('The Biochemistry of Clinical Medicine', 1970, pp. 48 and 55).

Danielpour et al., In Vitro Cell. & Dev. Biol. Jan. 1988, 24, pp. 42-52.

Feng et al. (Journal Dairy Science 78:2352-2357 (1995)).

Hallaway et al. (Proc. Nat'l. Acad. Sci. 85:10108-10112 (1989)).

Jiang et al. (Anticancer Research 22:2685-2692 (2002)).

Kresse et al (Magnetic Resonance in Medicine 40(2):236-242 (1998)).

Larson et al. (J. Nat'l. Cancer Inst. 64(1): 41-53 (1980)).

Mathias et al. (J. Nuclear Medicine 37(6): 1003-1008 (1996)).

Murphy (The Oncologist 3: 129-130 (1998)).

Parisot et al., British Journal of Cancer, 1999, vol. 79(5/6), pp. 693-700.

Patel et al. (Proc. Nat'l. Acad. Sci. 80:6518-6522 (1983)).

Reddel et al (Exp. Cell Research 161:277-284 (1985)).

Sato (Nippon Gan Chiryo Gakkaisi 28(10): 1716-1723 (1993)).

Wang et a.. (Anticancer Research 19:445-450 (1999)).

\* cited by examiner

ANTI-ESTROGEN AND IMMUNE MODULATOR COMBINATIONS FOR TREATING BREAST CANCER

CROSS-REFERENCE TO RELATED APPLICATIONS

This application claims the benefit under 35 U.S.C. §119 (e) of U.S. Provisional Patent Application No. 60/332,801 filed Nov. 14, 2001, and is a continuation-in-part of U.S. patent application Nos. 09/852,958 and 09/852,547, both filed May 10, 2001, the disclosure of each of which is hereby incorporated herein by reference.

STATEMENT REGARDING FEDERALLY SPONSORED RESEARCH OR DEVELOPMENT

Research leading to the present invention was supported in part by the federal government under Grant Nos. DAMD17-94-J-4473, DAMD17-98-1-8337 and DAMD17-99-19405 awarded by the Defense Department through the US Army Medical Research and Materiel Command, Breast Cancer Research Program. The United States government may have certain rights in the invention.

BACKGROUND OF THE INVENTION

1. Field of Invention

The present invention generally relates to methods and compositions for the use of tamoxifen and other anti-estrogenic compounds in combination with immune modulator agents (immunoglobulin inhibitors of estrogen responsive cancer cell growth), to treat or prevent breast cancer.

2. Description of Related Art

In 1896, a British physician named Beatson reported that öophorectomy had palliative effects for breast cancer patients (1). In 1905, Lett confirmed this observation with a larger patient trial (2). Clearly ovarian products were either directly or indirectly significant in breast cancer growth. From these earliest clinical observations, chemical and endocrine research continued and culminated in the identification of the primary ovarian/follicular agents responsible. The active agents proved to be a class of cholesterol derived steroid hormones now designated estrogens. In 1929 and 1930, Doisy and colleagues crystallized estrogens including estrone [3-hydroxy-estra-1,3,5(10)-trien-17-one] ($E_1$) from human pregnancy urine (3,12). Estradiol-17β[estra-1,3,5(10)-triene-3, 17β-diol] ($E_2$) was also isolated from sow follicular fluid (4). The remaining major estrogen, estriol [1,3,5-estratriene-3,16α,17β-triol] ($E_3$) has also been defined.

The relative potency of these three hormones is known today to be $E_2>E_1>>>>E_3$ (5). With regard to breast cancer cell growth, $E_2$ and $E_1$ are in the main considered the most physiologically relevant (6-9). Estriol is most likely relevant during pregnancy when the maternal plasma level is significantly elevated (10). During pregnancy, maternal $E_3$ is formed primarily as a placental conversion product of a steroid produced by the fetal adrenals. Breast cancers are not uncommon during pregnancy (18,22-25). However, all three estrogens are increased in pregnancy (10). In pregnant women, breast cancer is often diagnosed at a later stage (18). It may be that the elevated hormones during this time cause growth of developing breast cancer cells in pregnant females (19). Clearly, however, pregnancy has opposing effects on breast cancer development. On the one hand the increase in hormones can promote cancer cell growth (35). On the other hand, pregnancy and high hormones induce tissue differentiation that ultimately protects the tissue (20,21). Apparently the elevated estrogen levels in pregnancy explain the transient increase in short-term risk of breast cancer following term pregnancy (19). The results of several studies indicate that all three of the estrogenic steroid hormones (i.e. $E_2$, $E_1$ and $E_3$) are important in breast cancer risk in humans (26-28).

The biosynthesis and metabolism of estrogens and estrogen-related steroid hormones has been reviewed (11). The majority of plasma $E_2$ and $E_1$ is synthesized and secreted by cells of the ovarian follicle (29,30). The biochemical synthetic pathway begins with conversion of cholesterol to progesterone, followed by modification of the progestin to form androgens or androgen-like steroids. To form all three types of estrogen, the cholesterol origin "A" ring of "androgens" must be converted to a phenolic structure by the action of aromatases. These key enzymes in the biosynthesis of estrogens are located in the endoplasmic reticulum of ovarian cells.

Estrogens undergo a variety of metabolic transformations including hyroxylations, methylations and reduction. Also, the estrogens are converted to more water-soluble, biologically inactive, glucuronide and sulfate conjugates by the liver. The conjugates are excreted into urine and bile. Earlier studies indicated that estrogen conjugates (e.g. estrone sulfate) might serve as sources of free estrogen in breast cancer cells possessing the appropriate cleaving enzyme(s) to form free steroid (31). More recent work (32-34) indicates this is unlikely, based on tissue culture studies with eight different $ER^+$ cell lines. Estrogen sulfates and glucuronides are cleaved by intestinal flora to regenerate free estrogens that again appear in the plasma and urine via the enterohepatic circulation (36). A high fiber-low fat diet tends to decrease this process. Other intestinal microbial processes also convert inactive estrogen metabolites to active steroid hormones (37). Thus, recycling of estrogens is entirely possible.

However, the sites of synthesis of estrogenic substances in the body are not limited to the ovary (13). While it is understood with premenopausal women that estrogens are primarily of ovarian origin, this is not the case in postmenopausal females (38-41). The question is "what is the origin(s) of estrogens in the postmenopausal female"? This is important because breast cancer rates are much higher in postmenopausal women (42) even though estrogen levels are declining Nonetheless, 80 or 90% of breast cancers in postmenopausal women are $ER^+$ (43), implying they are estrogen growth promoted. This paradox can be explained in part by the suggestion that postmenopausal women with higher risk of developing breast cancer show relatively higher concentrations of endogenous estradiol (44). Also, it is now very clear that adrenal androgenic steroids can be converted to estrogens via the action of aromatases located in mammalian tissues (45). Its activity provides a significant portion of the plasma estrogens even in postmenopausal women (38-41). Aromatase activity has a broad tissue distribution in mammals (45). However, in human women after menopause, adipose tissue is the primary source of endogenous estrogens (46,47). Indeed, obesity is positively correlated with breast cancer (48). Also, aromatase is present in breast tissue and cells and represents an "intracrine" source of stimulating steroid hormone (49). Because of the major role of aromatase in generating breast cancer promoting estrogens in postmenopausal women, a series of aromatase inhibitors has been developed and are now in use as pharmaceutical products or are in and clinical trials as breast cancer treatments (41).

The question of how estrogens regulate target tissue gene expression and growth is of great consequence to this discussion. In 1962, Jensen & Jacobsen (14) came to the conclusion that estrogens acted on sex steroid hormone target tissues via specific cellular receptors. By 1972 to 1974, this research was sufficiently advanced to outline the mechanisms of estrogen action as mediated by an intracellular receptor (15-17). For several years, intense study has proceeded and has been reported in nearly 20 thousand publications (PubMed literature search of "estrogen receptors"). In 1986, the molecular cloning of the original estrogen receptor, now designated ERα, was reported (50,51). This 64-kDalton protein is functionally and structurally related to other receptors and has been classified as a member of the steroid and thyroid hormone superfamily (52). Today, these similar receptors include those for androgens, corticosteroids, progestins, thyroid hormones, vitamin D and retinoic acid.

Although for several years ERα was acknowledged as the only estrogen receptor, variants of it were being identified (55,56). However, in 1995, another type of estrogen receptor, designated ERβ, was cloned from a rat prostate and ovary (57). This initiated a boom of new activity to define the function and properties of ERβ (58,60,61). Indeed, the results suggest that the role of estrogens in male accessory organ function deserves renewed study (58). The characteristics and properties of ERα versus ERβ have been reviewed (58,61, 63). For the purposes of this disclosure, it should be noted that the binding affinities of both receptors are approximately equal (61). This was expected. However, one startling fact has surfaced. Mice gene knockout experiments for both ERα (62) and ERβ (60) have confirmed developmental functions for both of these receptors, but have fallen short of providing conclusive evidence that either receptor regulates growth (58). In fact, transfection of ER⁻ cells with a functional ERα led to an estrogen-induced inhibition of cell growth (59). There is a possibility that ERα is a receptor regulating expression of differentiated functions. It is well recognized that growth and differentiation are opposing cell functional states. Differentiated cells divide only slowly if at all. This issue has been reviewed in detail in recent U.S. patent application Nos. 09/852,547 and 09/852,958 and in International Patent Application Nos. PCT/US01/15171 (WO 01/86307) and PCT/US01/15183 (WO 01/85210), also identified in the list of References, below, as items 53 and 54, and hereby incorporated herein by reference). This led to the proposal in those applications that there is another growth regulating estrogen receptor, tentatively designated ERγ (53,54).

The characteristics of ERγ are that it binds estrogens with 10 to 100-fold higher affinities than ERα or ERβ. Furthermore, it is proposed that this receptor is a new gene that is expressed in all estrogen growth responsive target tissues. Data obtained indicate that this receptor is present in eight well-known estrogen responsive tumor cell lines derived from four tissues and three species including human (32-34, 53,54).

However, there exist potential alternatives regarding the identity of ERγ. Investigators have cloned two ERα-like "orphan receptors" with unknown functions (64,65). Other forms of estrogen receptors appear to arise as gene product splice variants (58,66). Those with major deletions of the hormone binding domain or the DNA binding domain may be expected to be inactive with respect to estrogen induced growth of breast cancer cells. The function of most of the other types of known variants remains to be established.

Another potentially significant variant has been identified. It is a point mutation that affects the border of the hinge-hormone-binding domains (67). This mutation was found in 34% of a series of 59 specimens of premalignant hyperplasia. Transfection of this mutated ERα caused MCF-7 human breast cancer cells to respond to lower concentrations of estrogen in culture. The full implications of this mutation await more study, but it is clear from the results available at this time, and those presented in the above-identified patent applications (53,54) and other recent publications (32-34), that MCF-7 as well as T47D and ZR-75-1 ER⁺ breast cancer cells respond to very low concentrations of $E_2$ even without transfection of the mutated ERα. It may be possible that the hypersensitive mutated receptor (67) is present in all ER⁺ cell types including those from rat mammary and rat pituitary tumors as well as from estrogen-induced kidney tumor cells from Syrian hamster (32-34). This means that a specific mechanism must exist for formation of this receptor in target tissue cells, or that this receptor is derived from a new gene. The latter possibility implies that the response of ER⁺ cells to very low concentrations of $E_2$ involves the proposed new ERγ (53,54).

The currently available knowledge about estrogen function and estrogen receptors has led to one of the most common treatments for disseminated and/or local ER⁺ breast cancer, especially in postmenopausal women. Today, selective estrogen receptor modulators (SERMs) are the compounds of choice (68). The mechanism of action of these drugs is to block the growth promoting action of estrogens at the cellular/receptor level, no matter whether the sex steroid hormones are delivered systemically or formed locally in breast tissue via aromatase action on adrenal steroid precursors. Hence, these drugs are classified as anti-estrogens. As a general mechanism of action, anti-estrogens are thought to interfere with the binding of natural estrogens to the growth promoting estrogen receptor(s).

The first potent anti-estrogen developed 1958 was MER-25 or ethamoxytriphetol (76). It then was used to derive clomiphene (77) which is now used to treat amenorrhea. Clomiphene was then modified to give rise to tamoxifen (78). Although several anti-estrogens have been developed, only two are currently FDA approved for treatment of human breast cancer. These are tamoxifen and toremifene. These, and idoxifene and droloxifene, are triphenylethylene derivatives. Notably, the toremifene structure differs from tamoxifen by only a single chlorine atom (69). Since its approval in 1977, tamoxifen has been the SERM of choice for treatment of ER⁺ breast cancer worldwide (70). Tamoxifen is classified as a "mixed" anti-estrogen because it displays both antagonistic properties (i.e. inhibits breast cancer cell growth) and agnostic properties (i.e. stimulates endometrial cell growth and tumor development) (71).

The action of the anti-estrogens is reversed by lower concentrations of the natural estrogens (53,54). The affinity of tamoxifen for the estrogen receptor is 10 to 100-fold less than that of $E_2$. This is commonly recognized throughout the endocrine cancer field. It is therefore useful to suppress natural estrogens along with application of tamoxifen treatment. This fact is often not recognized clinically. Postmenopausal women are not completely devoid of estrogens. Tamoxifen effectiveness is reduced by residual estrogenic steroid hormones. It is also reduced by the tamoxifen induced elevation of DHEA, $E_2$ and $E_1$ (81-83). This is an unfortunate side effect of using this drug alone.

One of the commonly cited facts concerning tamoxifen is that it acts at cellular sites separate from the estrogen receptor. It is known to influence such cellular activities as protein kinase C as well as several other cellular mechanisms including those related to apoptosis (72). Although non-steroid hormone receptor directed actions are usually considered undesirable, certain very recent co-owned patent disclosures (53,54) describe targeting a non-steroid hormone receptor with new drug combinations whose actions are based on anti-estrogen augmentation/mimicking of the inhibition of growth of ER$^+$ breast cancer cells by the immunoglobulins IgA and IgM of the natural secretory immune system. As described (53,54), the secretory immune system acts as a paracrine negative regulator of ER$^+$ breast cancer cell growth. Employing new serum-free defined culture assay methods (53,54), tamoxifen was shown to mimic the inhibition caused by IgA or IgM in the complete absence of estrogens. This new tamoxifen function represents a clear departure from previous thought concerning how this "mixed function" anti-estrogen acts. Previously, other investigators had reported that tamoxifen inhibited growth factor dependent proliferation of human breast cancer cells in cultures devoid of estrogens and estrogen-like agents (73). However, there was no indication at that time that this anti-estrogen was capable of acting by mimicking the growth inhibitory effects of the natural secretory immune system immunoglobulins IgA, IgM and IgG1.

Another class of anti-estrogens is defined as "pure" because they only affect growth via interaction with estrogen receptors (71). The pure anti-estrogens were discovered about 15 years ago (74). Currently, five compounds are under intense investigation (71). They are abbreviated ICI 164384, ICI 182780, EM-800, RU 58688 and EM-139 (71). Two of these, ICI 164384 and ICI 182780 are in clinical trials. Because tamoxifen resistance develops with time (75), the pure anti-estrogens are thought to be useful as second-line therapies after tamoxifen failure (71). Furthermore, pure anti-estrogens are thought useful because they cause no increase in endometrial cancer (71).

However, the pure anti-estrogens have marked deleterious effects on the cardiovascular and skeletal systems (71), and their usefulness is yet to be established. There remains a need for effective anti-estrogens and for combination therapies of tamoxifen or tamoxifen-like drugs and the "pure" anti-estrogens that may be more effective than either class of drug alone.

SUMMARY OF PREFERRED EMBODIMENTS

New compositions and methods are provided which advantageously employ compounds having a newly defined immune modulating function, or which have the ability to mimic that immune modulating function, or a combination of such compounds. For the purposes of the present disclosure, the terms "immune mimic," "immune modulating," "immune modulator," "immune modulation," "immune control," "immune inhibition," "immune suppressor," and the like, refer in most instances to the newly identified cancer cell growth (i.e., proliferation) inhibitory effect of the secretory immune system (i.e., dimeric/polymeric IgA and pentameric IgM) that is mediated by a newly identified Poly-Ig receptor or Poly-Ig-like receptor (also classified as an Fc-like receptor), and not to the usual antibody/antigen recognition based immune function of the immune system. In this context, the terms "immune modulation" or "immune enhancement" refer especially to the modulation or enhancement of these cell growth inhibitory immunoglobulins of the secretory immune system. The term "immune mimic" refers to a substance (e.g., tamoxifen) that can function in a similar manner to an immunoglobulin inhibitor of cell growth. In some instances, however, reference is also made herein to "natural immune inhibition," "immune enhancer," "immune modulator," "immune system," "immune therapy," and "immune response," and the like, in which the conventional meanings of those terms are intended and the context so indicates, especially when prior art methods, compounds and compositions are described. Hereinafter, an indication has been made in appropriate instances whether a conventional definition or the "new" meaning, or both, is intended.

In some aspects of the present invention, tamoxifen is used as a breast cancer treatment taking advantage of its newly identified function as an immune mimic instead of an anti-estrogen. That tamoxifen is a mixed anti-estrogen is well known. It not only binds to cellular estrogen receptors, but it also has other unrelated sites of cellular action. This new function for tamoxifen makes possible new combination therapies as well as new diagnostic methods to determine whether breast or other mucosal origin cancers are expected to be susceptible to these therapies. It is concluded that combination therapies of tamoxifen and the "pure" anti-estrogens may be more effective than either class of drug alone.

Tamoxifen treatment alone has several positive aspects as well as a number of negatives. The negatives can be overcome by placing this well known anti-estrogen in combinations with other compounds. The preferred combinations represent those that permit the mixture to act more effectively than the individual component alone. The combinations may include two or more breast cancer treatment drugs, some of which are classified as "pure" anti-estrogens while others are defined as immune modulators.

In accordance with certain embodiments of the present invention, a new tamoxifen-based therapeutic method is provided, in which tamoxifen acts as an immune inhibitor mimic ("immune mimic"). The method preferably includes employing a new diagnostic test to identify breast cancer cells expressing the inhibitor-mediating receptor (a Poly-Ig receptor or Poly-Ig like receptor), also classified as an Fc-like receptor, as an indication of sensitivity to cell growth inhibition by tamoxifen.

In accordance with another embodiment, the above-described tamoxifen therapy and diagnostic testing method is extended to mucosal cancers other than breast, including those of the prostate, colon, kidney, bladder, lung, pancreas, nasopharynx, ovary, endometrium, vagina, and cervix.

In still other embodiments, combinations of tamoxifen and aromatase inhibitors are employed to treat breast and gynecologic cancers. In some embodiments, tamoxifen and a "pure" anti-estrogen compound are combined for treating breast and gynecologic cancers.

Some embodiments of the present invention provide compositions or therapeutic methods using chemically modified MER-25 to treat secretory immune system related cancers. In some embodiments, MER-25 or modified MER-25 is combined with progesterone or another hormone for treating breast cancer. Modified MER-25 or derivative compounds of MER-25 that may have satisfactory anti-estrogenic or immune mimicking activity include methylated, alkylated, benzylated, halogenated, unsaturations, altered charge properties, and conformationally altered or stereoisomers of MER-25.

In certain embodiments, combinations of tamoxifen and levamisole are used as an immune mimic and immune modulator to treat breast and other mucosal cancers, including colon cancer. In certain embodiments, combinations of tamoxifen and imiquimod are used as an immune mimic and immune modulator to treat breast and other mucosal cancers. In certain embodiments, tamoxifen and OK-432 (picibanil) are used as an immune mimic and immune modulator to treat breast and other mucosal cancers.

Certain embodiments of the present invention provide compositions or therapeutic methods employing a combination of tamoxifen and DHEA (dehydroepiandrosterone) as an immune mimic and immune modulator to treat breast and other mucosal cancers. In certain embodiments, a therapeutic method is provided in which tamoxifen and an Fc-like receptor gene therapy are used together to treat breast and other mucosal cancers.

In still other embodiments of the invention, methods are provided for identifying anti-estrogenic compounds or for evaluating modified forms of existing compounds that might be more effective anti-estrogenic agents. These methods employ cell growth assays that, preferably, use certain serum-containing or serum-free media. In some embodiments, methods are provided for screening new compounds and for determining how combinations of compounds act on cells directly. These and other embodiments, features and advantages of the present invention will become apparent with reference to the following description.

DETAILED DESCRIPTION OF PREFERRED EMBODIMENTS

Example 1

Tamoxifen Therapy and New Diagnostic Test for Immune Modulation Applications with Breast Cancer Co-pending U.S. patent application Ser. Nos. 09/852,958 and 09/852,547, PCT Published Application Nos. WO 01/86307 and WO 01/85210, establish that tamoxifen mimics the cell growth inhibitory actions of the secretory immune system immunoglobulins IgA and IgM (53, 54). The disclosure of those applications are hereby incorporated herein by reference. Specifically, in WO 01/86307, examples 18, 19, 20, 21, and 22 (pages 110-129) and their accompanying figures and tables. The immunoglobulin action is mediated by a Poly-Ig receptor or a Poly-Ig-like receptor (also classified as an Fc-like receptor) that is identified by antibody raised against the extracellular five domains commonly called the "secretory component" (SC) (86). Those breast cancer cells expressing this Fc-like receptor are sensitive to inhibition by tamoxifen. Those cells not expressing the Fc-like receptor are not tamoxifen sensitive. Because the analysis can be done in completely serum-free defined medium (53,54) without estrogens, it is concluded that tamoxifen acts to mimic the Fc-like receptor mediated inhibition of cell growth by secretory immune system IgA and IgM. Using immunohistochemical analysis methods (88), breast cancer specimens will be examined for SC positive receptors. It has already been demonstrated that this methodology will identify breast cancers at the early stage when they are expressing an SC detectable receptor (87). These tumors are candidates for immune mimicking regulation. Those tumors that are Fc-like receptor positive are candidates for tamoxifen therapy or combined therapy with tamoxifen and the other agents described below. As a specific test is developed to detect the ERγ, the use of double label fluorescence will permit very accurate determination of patients that are strong candidates for the therapies described.

It is expected that tamoxifen inhibits breast cancer cell growth not by interaction with the commonly recognized ERα or ERβ but instead with the ERγ (53,54). The direct histochemical measurement of ERγ is expected to significantly increase the reliability of the decision to initiate anti-estrogen therapy. Further, the identification of ERγ will permit reanalysis of existing and new compounds for anti-ERγ activity. This approach can be expected to significantly advance how new SERMs are selected.

Example 2

Tamoxifen Therapy and New Diagnostic Test for Immune Modulation Applications with Other Mucosal Cancers Including Prostate, Colon, Kidney, Bladder Lung, Pancreas, Nasopharynx, Ovarian, Endometrial, Vaginal and Cervical Cancer The analysis outlined in Example 1 will be used to determine the application of the tamoxifen-based therapies to tumors arising from other mucosal tissues. Since the same secretory immune system is functional in all of the tissues (prostate, colon, kidney, bladder, lung, pancreas, nasopharynx, ovary, endometrium, vagina and cervix), the immunohistochemical analysis for SC detectable Fc-like receptor can be conducted. It has already been shown (89) that colon cancers progress through stages in which the SC is expressed (i.e. early differentiated tumors) to stages in which there is little or no detectable SC (i.e. late malignancy stage). Tamoxifen and/or the combinations described will be used to treat Fc-like receptor positive (FcLR$^+$) tumors by the new protocols. This new approach is expected to provide an expanded rationale for the use of tamoxifen to treat cancers not yet recognized as sensitive to this immune mimicking anti-estrogen. Further, as a test for ERγ is developed, it can be used to further refine the tumor types susceptible to the new modes of tamoxifen combination therapies.

An entirely new function is proposed for the well-known drug tamoxifen, in which tamoxifen mimics the immune system effects on ER$^+$ cancers, thereby inhibiting growth. It is believed that the estrogen reverses these effects, not as a consequence of interaction with the classical ERα, but as a consequence of the ERγ. This mechanism is closely parallel to that observed with IgA/IgM and $E_2$, disclosed in U.S. patent application Ser. No. 09/852,547 incorporated herein by reference. Prior to the present invention, tamoxifen has never been linked to growth regulatory changes in the secretory immune system nor has there been any suggestion that tamoxifen in any way mimics the inhibitory action of IgA/IgM on mucosal cells. Accordingly, certain embodiments of the present invention offer new uses for tamoxifen based on diagnostic testing to identify human breast, prostate, colon and other mucosal cancers that are Poly-Ig receptor/secretory component positive. For example, such identification could be determined by immunohistochemistry or radioimmunoassay or other suitable tests that have clinical applicability. Those tissues determined to be Poly-Ig receptor/secretory component positive are then candidates for tamoxifen treatment alone or in conjunction with other treatment modalities.

Example 3

Combinations of Tamoxifen and Aromatase Inhibitors to Treat Breast and Gynecologic Cancers It is proposed that simultaneous treatment with aromatase inhibitors and tamoxifen will be more effective than either drug alone. The therapeutic potential of this new combination is all the more significant in view of the fact that aromatase inhibitors do not completely inhibit estrogen synthesis. An unfortunate side effect of tamoxifen treatment is that it increases the concentration of estrogens in the plasma, which will have a marked effect on reducing the potency of tamoxifen as an anti-estrogen. The simultaneous use of aromatase inhibitors is expected to suppress this estrogen inductive effect and therefore may help to resolve the problem of escape of tumors from tamoxifen inhibition. In conventional therapies, tamoxifen resistance is currently thought to be a major problem with longer-term tamoxifen treatment. As additional tumor types beyond breast are identified as tamoxifen sensitive (e.g. endometrial, ovarian, vaginal, cervical and possibly prostate), the combined tamoxifen-aromatase inhibitor therapy will have even broader application than is recognized today for either drug.

Example 4

Combinations of Tamoxifen and Pure Anti-Estrogens to Treat Breast and Gynecologic Cancers The negative aspect of the current "pure" anti-estrogens discussed above is that they deplete the body of estrogen action so effectively that there are major cardiovascular and skeletal problems. However, by using the combination of tamoxifen and the "pure" anti-estrogens, the agonist action of tamoxifen can be expected to reduce this problem without supplying unwanted natural estrogens. Tamoxifen has positive effects on both the cardiovascular system and bone. Furthermore, it is expected that this combination will also reduce the problem of induction of endometrial cancers thought today to be a problem with the use of tamoxifen alone. Hence, the combination reduces major negative aspects seen with each drug alone. The balance of the two components can be varied to achieve specific end points.

Example 5

Use of Chemically Modified MER-25 to Treat Secretory Immune System Related Cancers MER-25 is an anti-estrogen by virtue of its inhibitory effects on estrogen target tissues. It also has the benefit that it does not interact with the estrogen receptor to accomplish its action (79). The advantage of MER-25 (or its modified forms) is that systemic or locally produced estrogens will not interfere. Thus, it can be used with ER$^+$ pre- and postmenopausal women without concern for suppression of endogenous estrogen levels. The results available support the present suggestion that MER-25 may mimic the immune activity of IgA and IgM even more strongly than tamoxifen.

Early anti-estrogens such as MER-25 were by-passed by previous investigators because of their potency and adverse side effects. Although MER-25 has many desirable properties as an anti-estrogen, it has been reported to be too toxic for use in humans (78). However, if MER-25 and related compounds can be modified to achieve high levels of immune modulation without the serious side effects, this will open additional new avenues of breast cancer therapy.

Accordingly, the chemical structure will be modified particularly in the O—C—C—N segment of the side chain to change the conformation and to prevent hydrogen bonding with neighboring hydroxyl groups (80). Only limited modifications in MER-25 have been sought (84). Other chemical changes in the structure are expected to attenuate the side effects considered most severe. Computer based molecular modeling will be used to develop the chemical modifications. The modifications are expected to include, for example, methylation, halogenation, unsaturations, alterations on charged groups, changes in conformation and selection of stable stereoisomers of the MER-25 structure. The chemically modified forms will be evaluated for anti-estrogenic activity using both the serum-containing and serum-free assay methods described in co-owned U.S. and PCT patent applications (53,54), incorporated herein by reference. This is a rapid and effective method of determining when a derivative has been obtained that still retains the desired potency against estrogen target cells in culture but cannot be reversed by exogenous estrogens in culture. Those that are effective under the strict tests outlined (53,54) will be tested for in vivo anti-tumor activity using rat mammary and pituitary models as well as with xenografts of human breast cancer cell lines in athymic nude mice.

Example 6

Combinations of MER-25 and Modified MER-25 with Progesterone and Other Hormones

The undesirable side effects of MER-25 and chemically modified forms may also be attenuated by simultaneous treatment with progesterone. In other studies, it has been shown that eating behavior and body weight regulation are affected by MER-25 (85). The administration of progesterone in rats corrected those side effects. Thus, at least some adverse properties in vivo may be due to altered hormonal influences. Administration of MER-25, and derivative compounds, will be evaluated for causation of endocrine changes. Any changes identified will be corrected by simultaneous application of the appropriate hormone(s). MER-25 or one of its derivatives may influence, for example, pituitary hormone secretion, thyroid hormones, adrenal hormones and/or neurogenic amines. Cytokines are also included in this group. Such changes are expected to yield the severe side effects reported (78). Accordingly, a hormone derived from pituitary, adrenals or thyroid, or a cytokine or a neurogenic hormone may be administered together with MER-25 or a modified form of MER-25 to deter the occurrence of side effects from the drug.

Example 7

Combination Tamoxifen and Levamisole as Immune Mimic and Immune Modulator to Treat Breast and Other Mucosal Cancers Including Colon Levamisole is known to be immunoregulatory at multiple levels (90). It is known to enhance an impaired immune system (91). Levamisole is currently used to treat Stage III colon cancer, and is recognized to be an immunostimulant, in the conventional sense, to assist the natural immune system (92). Drawing from the inventor's prior observations that increased secretory immunoglobulins IgA and IgM are not only cytostatic for breast cancer cells, but also cytotoxic, therapies that enhance immune function, increasing the presence of these secretory immunoglobulins in particular, are thus expected to be beneficial. It has been shown by others that a general elevation of the immune system by levamisole can retard colon cancer, but is not completely effective. The addition of tamoxifen is expected to enhance cancer cell death via apoptosis mechanisms. The diagnostic test for SC outlined above can be used to decide which patients should receive a combined levamisole/tamoxifen therapy.

Together, the combination of levamisole and tamoxifen for breast cancer is expected to have effects beyond that achievable with each compound alone. Levamisole will enhance the natural immune inhibition of breast cancer growth while tamoxifen offers an additional direct cellular effect. This combination approaches therapy from two different aspects of regulation. The use of levamisole to treat breast cancer is a new application, particularly when placed in combination with tamoxifen. Other components of preferred therapeutic compositions include aromatase inhibitors and/or "pure" anti-estrogens.

Example 8

Combination Tamoxifen and Imiquimod as Immune Mimic and Immune Modulator to Treat Breast and Other Mucosal Cancers Imiquimod is a conventional immune enhancer that is effective both as a topical preparation and when administered orally (93,94). The known use of this compound in breast cancer therapy is based on the action of interferon which is induced by imiquimod. The drug alone has only limited long term effects. Imiquimod therapy is expected to be highly effective in combination with an anti-estrogen such as tamoxifen or a new MER-25 derivative. The elevation of interferon affects the immune system as well as having potential effects directly on breast cancer cells. The addition of tamoxifen is expected to enhance any effects of interferon. This combination has three possible cytostatic/cytotoxic modes. First is the direct effect of the anti-estrogen. Second is an immune enhancing action of imiquimod, which is expected to include enhancement of the secretory immunoglobulin inhibitors of cancer cell growth. Third is the direct cytotoxic effect of interferon. This modality may be enhanced by measurement of the interferon receptor in breast specimens along with the Fc-like receptor.

Example 9

Combination Tamoxifen and OK-432 (Picibanil) as Immune Mimic and Immune Modulator to Treat Breast and Other Mucosal Cancers Ok-432 (Picibanil) is a streptococcal preparation that has a strong immune modulating effect (95), employing the conventional meaning of "immune modulating," which generally refers to the antibody/antigen recognition function of the immune system. The active moiety of this preparation has not been identified. This preparation cannot be delivered orally. It has been used in breast cancer as intratumor injections (96). In those prior studies, the results were mixed but additional results from cell culture suggest that a combination with an anti-estrogen may have greater effect than OK-432 alone (97). Another route to administration of OK-432 is intrapleural administration, which was evaluated as a treatment for breast malignancy in pleural effusions (98). The results of the conventional immune therapy alone on disseminated breast cancer were encouraging. It is now proposed that the combination of OK-432 with tamoxifen or an aromatase inhibitor will provide additional benefits and have anti-cancer effects beyond those that could have previously been predicted for OK-432 and tamoxifen. The role of OK-432 may be direct on tumor cells, or may involve a critical conventional immune response that then suppresses tumor cell growth. An additional possible use of this preparation may be as an oral challenge to develop mucosal immunity as described (53,54). This route of administration and development of mucosal immunity represents an entirely new approach to the use of this immune modulator.

Example 10

Combination Tamoxifen and DHEA (Dehydroepiandrosterone) as Immune Mimic and Immune Modulator to Treat Breast and Other Mucosal Cancers One recent report (101) asks the question "is DHEA a panacea or snake oil"? The answer likely rests with proper experimental design. DHEA use must be critically evaluated to achieve meaningful results. For example, the use of DHEA as a conventional immune modulator has been evaluated in postmenopausal women (99). That report stated that evidence was clear that DHEA was a positive immune modulator in these females. Furthermore, it was considered useful that DHEA metabolism in breast yields androgens that likely act as inhibitors of breast cancer growth. However, the evidence with a combination of DHEA and the "pure" anti-estrogen EM-800 with ZR-75-1 breast cancer cell xenografts in athymic nude mice were not as encouraging (100). DHEA inhibited alone, and the "pure" anti-estrogen alone inhibited. These results are pointed out to demonstrate that the proposal of using the "mixed" anti-estrogen tamoxifen with DHEA has merit. Tamoxifen acts as a direct immune mimic, as described in Example 1, in addition to blocking the estrogen receptor. DHEA acts to stimulate the immune system and to deliver inhibitory androgens to breast cancer cells. It is believed that the conventional immune stimulatory action of DHEA will also serve to enhance the presence of the inhibitory secretory immunoglobulins. This multilevel approach is expected to be more effective than each of the compounds used alone. It is also expected to be more effective than use of a "pure" anti-estrogen with only one mechanism of action. In addition, this combination may be even more effective when an aromatase inhibitor is added. Indeed, but applying the immunohistochemical classifications outlined above, along with determining the androgen receptor content, the combination therapy has a strong rational basis. Today androgen receptors are rarely measured in specimens of female breast cancer.

Example 11

Combination Tamoxifen and Fc-Like Receptor Gene Therapy to Treat Breast and Other Mucosal Cancers Because tamoxifen is effective only with cells that express the Poly-Ig (Fc) receptor or a Poly-Ig-like (Fc) receptor, introduction of this receptor into cells lacking immune control offers an entirely new approach to treatment of breast and other mucosal cancers. Viral vectors bearing the DNA coding for the full length functional Fc-like receptor can be used to transform disseminated cancer such that the tumor cells regain sensitivity to tamoxifen. This is a significant concept because it permits activation of killing over a long duration and with multiple exposures to the virus plus tamoxifen. Since tamoxifen can typically be used over a five-year period, and viral infections repeated, this new approach has considerable promise and is supported by the recognized fact that all cancer cells will not be killed after even the first few viral infections. The properties of the receptor to be used have been described (53,54), and techniques for incorporating a desired DNA sequence into a suitable viral vector, and for transforming a population of cells are known and have been described in the literature.

Example 12

Use of Serum-Containing and Serum-Free Medium Assays to Define New Anti-Estrogenic Compounds or to Modify Existing Compounds to More Effective Agents The above-identified co-owned U.S and PCT patent applications (53,54), hereby incorporated herein by reference, describe two different types of assays that will be used to characterize new anti-estrogenic compounds and derivatives. One assay is done with $ER^+$ cell lines grown in medium supplemented with steroid hormone depleted serum. The serum is preferably prepared by either charcoal dextran extraction, or by XAD-4 resin treatment (53,54). Similar assays can be done under completely serum-free defined conditions. The results of the two assays can be compared directly. Several suitable cell lines for use in the assays are available from three different species and four different tissues (32-34), although another cell line that is capable of growing both in cell culture and when implanted into a compatible host could also be used. Use of steroid hormone depleted serum permits evaluation of its effect on the activity of the new compound. The presence of serum factors may alter activity and therefore indicate problems before initiation of time consuming and expensive animal testing.

REFERENCES (1) Beatson G T (1896) On treatment of inoperable cases of carcinoma of the mamma: suggestions for a new method of treatment with illustrative cases. Lancet (Part 1) July 11:104-107; (Part 2) July 18:162-165.
(2) Lett H (1905) An analysis of 99 cases of inoperable carcinoma of the breast treated by öophorectomy. Lancet January 28:227-228.
(3) Doisy E A, Veler C D & Thayer S (1929) Folliculin from urine of pregnant women. Am J Physiol 90:329-330.
(4) MacCorquodale D W, Thayer S A & Doisy E A (1936) The isolation of the principal estrogenic substance of liquor folliculi. J Biol Chem 115:435-448.
(5) Clark J H & Markaverich B M (1983) The agonistic and antagonistic effects of short acting estrogens: a review. Pharm Ther 21:429-453.
(6) Lippman M E, Monaco M E & Bolan G (1977) Effects of estrone, estradiol, and estriol on hormone responsive human breast cancer in long term tissue culture. Cancer Res 37:1901-1907.
(7) Jozan S, Moure C, Gillois M & Bayard F (1979) Effects of estrone on cell proliferation of human breast cancer (MCF-7) in long term tissue culture. J Steroid Biochem 10:341-342.
(8) Katzenellenbogen B S (1984) Biology and receptor interactions of estriol and estradiol derivatives in vitro and in vivo. J Steroid Biochem 20:1033-1037.
(9) Karey K P & Sirbasku D A (1988) Differential responsiveness of the human breast cancer cell lines MCF-7 and T47-D to growth factors and 17β-estradiol. Cancer Res 48:4083-4092.
(10) Freinkel N & Metzger B E (1992) Metabolic changes in pregnancy. In: Williams Textbook of Endocrinology, $8^{th}$ Edition, Wilson J D & Foster D W (eds), W B Saunders Company, Philadelphia, pp 993-1005.
(11) Gore-Langton E & Armstrong D T (1988) Folicular steroidogenesis and its control. In: The Physiology of Reproduction, Knobile E & Neill J D (Eds-in-chief), Raven Press, New York, pp 331-385.
(12) Doisy E A, Veler C D & Thayer S A (1930) The preparation of the crystalline ovarian hormone from the urine of pregnant women. Am J Physiol 86:499-509.
(13) Corner G W (1983) The sites of formation of estrogenic substances in the animal body. Physiol Rev 18:154-172.
(14) Jensen E V & Jacobsen H I (1962) Basic guides to the mechanism of estrogen action. Recent Prog Horm Res 18:387-414.
(15) Jensen E V & DeSombre E R (1972) Mechanism of action of the female sex hormones. Ann Rev Biochem 41:203-230.
(16) Jensen E V & DeSombre E R (1973) Estrogen-receptor interaction. Estrogenic hormones effect transformation of specific receptor proteins to a biochemically functional form. Science (Wash D.C.) 182:126-134.
(17) O'Malley B W & Means A R (1974) Female steroid hormones and target cell nuclei. Science (Wash D.C.) 183: 610-620.
(18) Gemignani M L & Petrek J A (2000) Breast cancer during pregnancy: diagnostic and therapeutic dilemmas. Adv Surg 34:273-286.
(19) Lambe M, Hsieh C-C, Trichopoulos D, Ekbom A, Pavia M & Adami H-O (1994) Transient increase in the risk of breast cancer after giving birth. N Eng J Med 331:5-9.
(20) Miller W R (1993) Hormonal factors and risk of breast cancer. Lancet 341:25-26.
(21) MacMahon B (1993) General Motors Cancer Research Prizewinners Laureates Lectures. Charles S. Mott Prize. Reproduction and cancer of the breast. Cancer 71:85-88.
(22) Ibrahim E M, Ezzat A A, Baloush A, Hussain Z H & Mohammed G H (2000) Pregnancy-associated breast cancer: a case-control study in a young population with high fertility rate. Med Oncol 17:293-300.
(23) Gwyn K & Theriault R (2001) Breast cancer during pregnancy. Oncology (Huntingt) 15:39-46; discussion 46.
(24) Moore H C & Foster R S Jr (2000) Semin Oncol 27:646-653.
(25) Gemignani M L, Petrek J A & Borgen P I (1999) Breast cancer and pregnancy. Surg Clin North Am 79:1157-1169.
(26) Key T J (1999) Serum oestradiol and breast cancer risk. Endocrine-Related Cancer 6:175-180.
(27) Persson I (2000) Estrogens in the causation of breast, endometrial and ovarian cancers—evidence and hypotheses from epidemiological findings. J Steroid Biochem Mol Biol 74:357-364.
(28) Hulka B S & Moorman P G (2001) Breast cancer: hormones and other risk factors. Maturitas 38:103-113; discussion 113-116.
(29) Ross G T & Vande Wiele R L (1974) Chapter 7: The Ovaries. In: Textbook of Endocrinology, $5^{th}$ Edition, Williams R H (ed), W B Saunders, Philadelphia, pp 368-422.
(30) Williams C L & Stancel G M (1995) Chapter 57: Estrogens and Progestins. In: Goodman & Gilman's The Pharmacological Basis of Therapeutics, $9^{th}$ Edition, Hardman J G & Limbird L E (Eds-in-Chief), McGraw-Hill, New York, pp 1411-1440.
(31) Vignon F, Terqui M, Westley B, Derocq D & Rochefort H (1980) Effects of plasma estrogen sulfates in mammary cancer cells. Endocrinology 106:1079-1086.
(32) Moreno-Cuevas J E & Sirbasku D A (2000) Estrogen mitogenic action. I. Demonstration of estrogen-dependent MTW9/Pl2 carcinogen-induced rat mammary tumor cell growth in serum-supplemented culture and technical implications. In Vitro Cell Dev Biol 36:410-427.
(33) Sirbasku D A & Moreno-Cuevas J E (2000) Estrogen mitogenic action. II. Negative regulation of the steroid hormone-responsive growth of cell lines derived from human and rodent target tissue tumors and conceptual implications. In Vitro Cell Dev Biol 36:428-446.

(34) Moreno-Cuevas J E & Sirbasku D A (2000) Estrogen mitogenic action. III. Is phenol red a "red herring"? In Vitro Cell Dev Biol 36:447-464.

(35) Petrek J A (1994) Breast cancer and pregnancy. J Natl Cancer Inst Monograph 16:113-121.

(36) Gorbach S L (1984) Estrogens, breast cancer, and intestinal flora. Rev Infect Dis Suppl 1:S85-S90.

(37) Axelson M & Sjovall J (1983) Formation of catechol estrogens by intestinal bacterial demethylation of 2-methoxyestrone. Biochim Biophys Acta 751:162-165.

(38) Simpson E R (2000) Role of aromatase in sex steroid action. J Mol Endocrinol 25:149-156.

(39) Longcope C (2001) Endocrine function of the postmenopausal ovary. J Soc Gynecol Investig 8 (suppl):S67-S68.

(40) Van Zonneveld P, Scheffer G J, Broekmans F J M & te Velde E R (2001) Hormones and reproductive aging. Maturitas 38:83-94.

(41) Kuerer H M, Buzdar A U & Singletary S E (2001) Biologic basis and evolving role of armoatase inhibitors in the management of invasive carcinoma of the breast. J Surg Oncol 77:139-147.

(42) Ries L A G, Kosary C L, Hankey B F et al (1999) "SEER Cancer Statistics Review, 1973-1996". Bethesda, Md.: National Cancer Institute.

(43) Diab S G, Elledge R M & Clark G M (2000) Tumor characteristics and clinical outcome of elderly women with breast cancer. J Natl Cancer Inst 92:550-556.

(44) Thomas H V, Reeves G K & Key T J (1997) Endogenous estrogen and postmenopausal breast cancer: a quantitative review. Cancer Causes Control 8:922-928.

(45) Conley A & Hinshelwood M (2001) Mammalian aromatases. 121:685-695.

(46) Siiteri P K & MacDonald P C (1973) Role of extraglandular oestrogen in human endocrinology. In: Handbook of Physiology, Volume 2, Greep R o & Astwood E B (eds) American Physiology Society, Washington D.C., pp 619-629.

(47) Simpson E R, Zhao Y, Agarwal V R, Michael M D et al (1997) Aromatase expression in health and disease. Recent Prog Horm Res 52:185-213.

(48) Huang Z, Hankinson S E, Colditz G A, Stampfer M J et al (1997) Dual effects of weight and weight gain on breast cancer risk. JAMA 278:1407-1411.

(49) Labrie F, Belanger A, Cusan L & Candas B (1997) J Clin Endocrinol Metab 82:2403-2409.

(50) Green S, Walter P, Kumar V Krust A et al (1986) Human oestrogen receptor cDNA: sequence, expression and homology to verb-A. Nature 320:134-139.

(51) Greene G L, Gilna P, Waterfield M, Baker A, Hort Y & Shine J (1986) Sequence and expression of the estrogen receptor complimentary DNA. Science (Wash D.C.) 231: 1150-1154.

(52) Evans R M (1988) The steroid and thyroid hormone receptor superfamily. Science (Wash D.C.) 240:889-895.

(53) Sirbasku, David A. "Compositions and Methods for the Diagnosis, Treatment and Prevention of Steroid Hormone Responsive Cancers" U.S. patent application No. 09/852,547 (U.S. Published application No. 20,020,006,630) and corresponding PCT Published Application No. WO 01/86307.

(54) Sirbasku, David A. "Compositions and Methods for Demonstrating Secretory Immune System Regulation of Steroid Hormone Responsive Cancer Cell Growth" U.S. patent Ser. No. 09/852,958 (U.S. Published application No. 20,020,012,954 and corresponding PCT Published Application No. WO 01/85210.

(55) Fuqua S A W, Fitzgerald S D, Chamness G C, Tandon A K et al (1991) A variant human breast tumor estrogen receptor with constitutive transcriptional activity. Cancer Res 51:105-109.

(56) Zhang Q-X, Borg A, Wolf D M, Oesterreich S & Fuqua S A W (1997) An estrogen receptor mutant with strong hormone-independent activity from metastatic breast cancer. Cancer Res 57:1244-1249.

(57) Kuiper G G, Enmark E, Pelto-Huikko M, Nilsson S & Gustafsson J-A (1996) Cloning of a novel receptor expressed in rat prostate and ovary. Proc Natl Acad Sci USA 93:5925-5930.

(58) Nilsson S, Makela S, Treuter E, Tujaque M et al (2001) Mechanisms of estrogen action. Physiol Rev 81:1535-1565.

(59) Zajchowski D A, Sager R & Webster L (1993) Estrogen inhibits the growth of estrogen receptor-negative, but not estrogen receptor-positive, human mammary epithelial cells expressing a recombinant estrogen receptor. Cancer Res 53:5004-5011.

(60) Gustafsson J-A & Warner M (2000) Estrogen receptor P in the breast: role in estrogen responsiveness and development of breast cancer. J Steroid Biochem Mol Biol 74:245-248.

(61) Dickson R B & Stancel G M (1999) Chapter 8: Estrogen receptor-mediated processes in normal and cancer cells. J Natl Cancer Inst Monographs No. 27:135-145.

(62) Couse J F & Korach K S (1999) Estrogen receptor null mice: what have we learned and where will they lead us? Endocr Rev 20:358-417.

(63) Couse J F, Curtis-Hewitt S & Korach K S (2000) Receptor null mice reveal contrasting roles for estrogen receptor cc and D in reproductive tissues. J Steroid Biochem Mol Biol 74:287-296.

(64) Giguere V, Yang N, Seui V & Evans R M (1988) Identification of a new class of steroid hormone receptors. Nature 331:91-94.

(65) Beato M & Klug J (2000) Steroid hormone receptors: an update. Human Reproduction Update 6:225-236.

(66) Hopp T & Fuqua S (1998) Estrogen receptor variants. J Mammary Gland Biol Neoplasia 3:73-83.

(67) Fuqua S A, Wiltschke C, Zhang Q X, Borg A et al (2000) A hypersensitive estrogen receptor alpha mutation in premalignant breast lesions. Cancer Res 60:4026-4029.

(68) Goldstein S R, Siddhanti S, Ciaccia A V & Plouffe L Jr (2000) A pharmacological review of selective oestrogen receptor modulators. Human Reprod Update 6:212-224.

(69) Buzdar A U & Hortobagyi G N (1998) Tamoxifen and toremifene in breast cancer: comparison of safety and efficacy. J Clin Oncol 16:348-353.

(70) Buzdar A U & Hortobagyi G (1998) Update on endocrine therapy for breast cancer. Clin Cancer Res 4:527-534.

(71) Hermenegildo C & Cano A (2000) Pure anti-estrogens. Human Reproduction Update 6:237-243.

(72) Mandlekar S & Kong A N (2001) Mechanism of tamoxifen-induced apoptosis. Apoptosis 6:469-477.

(73) Vignon F, Bouton M-M & Rochefort H (1987) Antiestrogens inhibit the mitogenic effect of growth factors on breast cancer cells in the total absence of estrogens. Biochem Biophys Res Commun 146:1502-1508.

(74) Wakeling A E & Bowler J (1987) Steroidal pure anti-estrogens. J Endocrinol 112:R7-R10.

(75) Jordan V C (1993) A current view of tamoxifen for the treatment and prevention of breast cancer. Br J Pharmacol 110:507-517.
(76) Lerner U, Holthaus F G & Thompson C R (1958) The non-steroidal estrogen antagonist (MER-25). Endocrinology 63:295-318.
(77) Greenblatt R B, Roy S, Mahesh V B et al (1962) Induction of ovulation. Am J Obstetrics Gynecology 84:900-909.
(78) Lerner L J & Jordan V C (1990) Development of anti-estrogens and their use in breast cancer. Cancer Res 50:4177-4189.
(79) Lyman S D & Jordan V C (1985) Possible mechanisms for the agonist actions of tamoxifen and the antagonist actions of MER-25 (ethamoxytriphetol) in mouse uterus. Biochem Pharmacol 34:2795-2806.
(80) Hossain M B, Symersky J, Neely S C, van der Helm D & Magarian R A (1993) Structure of 1-(4-[2-(diethylamino) ethoxy]phenyl)-2-(4-methoxyphenyl)-1-phenylethan-1-ol, the non-steroidal anti-estrogen MER-25. Acta Crystallogr 49:500-504.
(81) Lonning P e, Johannessen D C, Lien E A et at (1995) Influence of tamoxifen on sex hormones, gonadotrophins and sex hormone binding globulin in postmenopausal breast cancer patients. J Steroid Biochem Mol Biol 52:491-496.
(82) Geisler J, Haarstad H, Gunderson S et al (1995) Influence of treatment with the anti-estrogen 3-hydroxytamoxifen (droloxifene) on plasma sex hormone levels in postmenopausal patients with breast cancer. J Endocrinol 146:359-363.
(83) Lum S S, Woltering E A, Fletcher W S et al (1997) Changes in serum estrogen levels in women during tamoxifen therapy. Am J Surg 173:399-402.
(84) Clark E R & Jordan V C (1976) Oestrogenic, anti-oestrogenic and fertility effects of some triphenylethanes and triphenylethylenes related to ethamoxytriphetol (MER-25). Br J Pharmacol 57:487-493.
(85) Roy E J & Uade G N (1976) Estrogenic effects of an anti-estrogen, MER-25, on eating and body weight in rats. J Comp Physiol Psychol 90:156-166.
(86) Krajci P, Kvale D, Tasken K & Brandtzaeg P (1992) Molecular cloning and exonintron mapping of the gene encoding human transmembrane secretory component (the Poly-Ig receptor). Eur J Inmunol 22:2309-2315.
(87) Stern J E, Underdown B J, Crichlow R W & Wira C R (1985) Secretory component in breast cancer. Analysis of the levels in primary and metastatic disease. Cancer Immunol Immunother 19:226-230.
(88) Brandtzaeg P & Rognum T O (1984) Evaluation of nine different fixatives. 1. Preservation of immunoglobulin isotypes, J chain, and secretory component in human tissues. Path Res Pract 179:250-266.
(89) Krajci P, Meling G I, Andersen S N et al (1996) Secretory component mRNA and protein expression in colorectal adenomas and carcinomas. Br J Cancer 73:1503-1510.
(90) Goldstein G (1978) Mode of action of levamisole. J Rheumatol Suppl 4:143-148.
(91) Prakash M S, Rao V M & Reddy V (1998) Effect of levamisole on the immune status of malnourished children. J Trop Pediatrics 44:165-166.
(92) Holcombe R F, Li A & Stewart R M (1998) Levamisole and interleukin-2 for advanced malignancy. Biotherapy 11:255-258.
(93) Savage P, Horton V, Moore J et al (1996) A phase I trial clinical trial of imiquimod, an oral interferon inducer, administered daily. Br J Cancer 74:1482-1486.
(94) Witt P L, Ritch P S, Reding D et al (1993) Phase I trial of an oral immunomodularor and interferon inducer in cancer patients. Cancer Res 53:5176-5180.
(95) Chirigos M A (1992) Immunomodulators: current and future development and application. Thymus 19 (suppl): S7-S20.
(96) Takeda T, Kobayashi T, Monden T et al (1993) The effect of local immunotherapy for breast cancer using a mixture of OK-432 and fibrinogen supplemented with activated macrophages. Biotherapy 7:47-53.
(97) Aoyagi H, Eino Y, Takeo T et al (1997) Effects of OK-432 (picibanil) on estrogen receptors of MCF-7 cells and potentiation of antiproliferative effects of tamoxifen in combination with OK-432. Oncology 54:414-423.
(98) Kan N, Kodama H, Hori T et al (1993) Intrapleural adaptive immunotherapy for breast cancer patients with cytologically-confirmed malignant pleural effusions: an analysis of 67 patients in Kyoto and Shiga Prefecture, Japan. Breast Cancer Res Treat 27:203-210.
(99) Casson P R, Andersen R N, Herrod H G et al (1993) Oral dehydroepiandrosterone in physiologic doses modulates immune function in postmenopausal women. Am J Obstet Gynecol 169:1536-1539.
(100) Couillard S, Labrie C, Belanger A et al (1998) Effect of dehydroepiandrosterone and the anti-estrogen EM-800 on growth of human ZR-75-1 breast cancer xenografts. J Natl Cancer Inst 90:772-778.
(101) Sirrs S M & Bebb R A (1999) DHEA: panacea or snake oil? Can Fam Physician 45:1723-1728.

While the preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. For example, the foregoing descriptions primarily focus on the treatment and prevention of breast cancer in high-risk individuals, however the same or similar approaches can be employed to with respect to other types of cancers of mucosal tissues, including prostate, ovary, endometrium, cervix, vagina, colon, kidney, lung, pancreas and nasopharynx. Cancers of those tissues, together with breast cancer, account for 80% of all human cancer. The disclosures of all patents, patent applications and publications cited hereinabove are hereby incorporated herein by reference. The discussion of certain references in the Description of Related Art, above, is not an admission that they are prior art to the present invention, especially any references that may have a publication date after the priority date of this application.

What is claimed is:

1. A method of predicting susceptibility of a cancer patient to treatment with Tamoxifen, comprising:
    detecting the presence of a Poly-Ig receptor, or the (Fc) region thereof, in a sample from the cancer patient, wherein the detection of a Poly-Ig receptor, or the (Fc) region thereof, is indicative of said cancer patient being more susceptible to treatment with Tamoxifen as compared to a sample obtained from a second patient, wherein said sample from said second patient comprises an ER alpha+ breast cancer cell, and wherein said Poly-Ig– receptor, or the (Fc) region thereof, is not detected in said sample from said second patient,
    wherein said cancer patient sample comprises an ER alpha+ and Poly-Ig receptor+ breast cancer cell of mucosal origin.

2. The method of claim 1, wherein the presence of the (Fc) region of the poly-Ig receptor in said cancer patient sample is indicative of said cancer patient being more susceptible to treatment with Tamoxifen.

* * * * *